United States Patent [19]

Allum

[11] Patent Number: 6,063,046
[45] Date of Patent: May 16, 2000

[54] METHOD AND APPARATUS FOR THE DIAGNOSIS AND REHABILITATION OF BALANCE DISORDERS

[76] Inventor: John H. Allum, Hebel Str. 109, Basel, Switzerland, CH-4056

[21] Appl. No.: 09/057,868

[22] Filed: Apr. 9, 1998

Related U.S. Application Data

[60] Provisional application No. 60/043,859, Apr. 11, 1997.

[51] Int. Cl.[7] .................................................. A61B 5/103
[52] U.S. Cl. ............................................................. 600/595
[58] Field of Search .................................. 600/587, 594, 600/595

[56] References Cited

U.S. PATENT DOCUMENTS

| | | |
|---|---|---|
| 3,090,226 | 5/1963 | Corti et al. . |
| 4,092,663 | 5/1978 | Fletcher et al. . |
| 4,738,269 | 4/1988 | Nasher . |
| 4,817,633 | 4/1989 | McStravick et al. . |
| 4,830,024 | 5/1989 | Nashner et al. . |
| 4,848,358 | 7/1989 | Nitzan et al. . |
| 4,938,476 | 7/1990 | Brunelle et al. . |
| 5,052,406 | 10/1991 | Nashner . |
| 5,209,240 | 5/1993 | Jain et al. . |

(List continued on next page.)

FOREIGN PATENT DOCUMENTS

| | | |
|---|---|---|
| 3418873 A1 | 11/1985 | Germany . |
| WO 88/04909 | 7/1988 | WIPO . |

OTHER PUBLICATIONS

G.H. Begbie, "Some Problems of Postural Sway", in "Myotatic, Kinesthetic and Vestibular Mechanisms", pp. 80–104 (A.V.S. deReuck & Julie Knight, eds., 1967).

L.M. Nashner, "A Model Describing Vestibular Detection of Body Sway Motion", Acta Otolaryng 72, pp. 429–436, 1971.

E.V. Gurfinkel, "Physical Foundations of the Stabilography", Agressologie, 14, C, pp. 9–14, 1973.

J. Dichgans, et al., "Postural Sway In Normals and Atactic Patients: Analysis of the Stabilizing and Destabilizing Effects of Vision", Agressologie 17, C, pp. 15–24, 1976.

L.M. Nashner, "Adapting Reflexes Controlling the Human Posture", Exp. Brain Res., vol. 26, pp. 59–72, 1976.

S.H. Koozekanani, "On the Role of Dynamic Models in Quantitative Posturography", IEEE Trans. Biomed. Eng., vol. BME–27, No. 10, pp. 605–609, Oct., 1980.

F. Owen Black, et al., "Effects of Visual and Support Surface Orientation References Upon Postural Control in Vestibular Deficient Subjects", Acta Otolaryngol 95, pp. 199–210, 1983.

(List continued on next page.)

*Primary Examiner*—Cary O'Connor
*Assistant Examiner*—Pamela Wingood
*Attorney, Agent, or Firm*—Foley & Lardner

[57] ABSTRACT

A method and apparatus for the diagnosis and rehabilitation of abnormal human balance corrections. A subject is placed in a standing position on a support surface which can be moved in any combination of pitch and roll directions. Measurements of the balance response of the subject are made using, e.g., force transducers in the support surface (to measure changes in center-of-foot pressure or ankle torque), body sway sensors, such as velocity transducers, mounted on the subject's body (to measure body sway), and EMG electrodes, mounted over muscles on the left and right sides of the subject's body (to measure the electromyographic response of the subject's muscles). The response measures are displayed to an operator in a highly readable form along with response measures from a normal sample population. From the display of response measures, an operator or the system may diagnose the existence, cause (e.g., vestibular, proprioceptive, CNS lesion, or aphysiologic), and side (left or right) of a balance correction abnormality. Response measure information may be provided as feedback to the test subject in visual, auditory, tactile, or electro-vestibular form. A destabilizing virtual reality visual response measure feedback image may be provided using an imaging system mounted on a pair of light excluding eyewear.

42 Claims, 13 Drawing Sheets

U.S. PATENT DOCUMENTS

| | | |
|---|---|---|
| 5,281,957 | 1/1994 | Schoolman . |
| 5,303,715 | 4/1994 | Nashner et al. . |
| 5,337,757 | 8/1994 | Jain et al. . |
| 5,360,015 | 11/1994 | Heurte ........................................ 600/587 |
| 5,361,778 | 11/1994 | Seitz . |
| 5,368,042 | 11/1994 | O'Neal et al. . |
| 5,388,591 | 2/1995 | De Luca et al. ........................ 600/592 |
| 5,469,861 | 11/1995 | Piscopo et al. . |
| 5,551,445 | 9/1996 | Nashner . |
| 5,627,327 | 5/1997 | Zanakla . |
| 5,749,372 | 5/1998 | Allen et al. . |

OTHER PUBLICATIONS

Mary E. Tinetti, et al., "Fall Risk Index for Elderly Patients Based on Number of Chronic Disabilities", Am. J. Med., vol. 80, pp. 429–434, Mar., 1996.

F. Owen Black, et al., "Effects of Unilateral Loss of Vestibular Function on the Vestibulo–Ocular Reflex and Postural Control", Ann. Otol. Rhinol. Laryngol. 98, pp. 884–889, 1989.

Emily A. Keshner & John H.J. Allum, "Muscle Activation Patterns Coordinating Postural Stability from Head to Foot", In "Multiple Muscle Systems: Biomechanics and Movement Organization", pp. 481–497, (J.M. Winters & S.L–Y. Woo, eds., 1990).

Kamran Barin, "Dynamic Posturography: Analysis of Error In Force Plate Measurement of Postural Sway", IEEE Eng. in Med. Biol., vol. 11, No. 4, pp. 52–56, Dec., 1992.

D. Perennou, et al., "Optoelectronic assessment of upper body sway in erect posture: validation for 3–D stabilometry", in "Vestibular and neural front", pp. 57–60, (K. Taguchi, et al., eds., 1994).

Y. Ehara, et al., "Comparison of the performance of 3D camera systems", Gait & Posture, vol. 3, pp. 166–169, Sep., 1995.

Thomas E. Prieto, et al., "Measures of Postural Steadiness: Differences Between Healthy Young and Elderly Adults", IEEE Trans. Biomed. Eng., vol. 43, No. 9, pp. 956–966, Sep., 1996.

U.S. application No. 08/818,319, filed Mar. 14, 1997, pending, entitled Method and Apparatus for Angular Position and Velocity Based Determination of Body Sway For the Diagnosis and Rehabilitation of Balance of Gait Disorders, by John H. Allum, assigned to Group Art Unit 3736, Examiner M. Hindenberg.

METHOD AND APPARATUS FOR THE DIAGNOSIS AND REHABILITATION OF BALANCE DISORDERS

This application claims the benefit of U.S. Provisional Application No. 60/043,859, filed Apr. 11, 1997.

FIELD OF THE INVENTION

This invention pertains generally to methods and devices for performing non-invasive tests for the presence of abnormalities in the balance corrections of human subjects.

BACKGROUND OF THE INVENTION

Individuals who suffer from a balance control disorder are abnormally prone to falling and have poor gait control when walking or engaging in other movement tasks. A balance control disorder may be the result of a wide variety of sensory and/or motor disorders that impair the posture and equilibrium control of the subject. Balance control disorders may be caused by vestibular, proprioceptive, central nervous system (CNS) or other defects. Vestibular defects are abnormalities related to the part of the auditory nerve in the inner ear that carries sensory information related to body equilibrium. Proprioceptive defects are abnormalities in the stimuli provided to or received by a subject's muscles to maintain equilibrium control. Balance control disorders may affect both sides (left and right) of a subject, or may be manifested as a greater instability in one direction.

In order to make a correct assessment of a subject's balance control, and thereby to take remedial measures, an examining physician, or physical therapist, may determine the subject's balance control ability for a number of motor tasks, such as standing, getting up out of a chair, walking down steps, etc. By observing the subject performing such motor tasks, the physician may be able to determine if the subject's balance control is within normal limits and, if not, how best to bring balance control near or within normal limits again. However, to provide a more accurate and objective assessment of the individual's sensory and motor components of posture and equilibrium, a test system which provides an objective quantifiable assessment of balance control is required.

Quantitative information on the human sense of balance can be obtained using a variety of methods and devices. Quantitative information on the efficacy of the human sense of balance can be obtained by the electrophysiological measurement of eye movements or of the postural responses of the limbs. A balance control deficit is indicated if a response is outside of the limits expected for individuals having a normal balance function. Quantitative postural information may also be obtained by measuring contractile activity of the muscles generating the internal body forces for maintaining the equilibrium position using electromyographic (EMG) recordings.

Balance control defects are often quantified by recording body sway, i.e., the displacement of the body from the equilibrium position. Quantification of the postural sway of a subject is known as "stabilometry" or "posturography". One method for quantifying balance disorders involves the measurement of body sway in terms of displacement of the center of foot pressure (CFP), sometimes termed "center of force", generated by the inherent instability of a test subject standing on a fixed support surface. CFP is computed from the signals provided by force transducers which are typically embedded in the four corners of the support surface. The force transducer outputs are employed to obtain a projection, on the support surface platform, of the resultant forces acting at the subject's center of gravity. An anterior-posterior, front-to-back, projection is obtained by assuming that the difference between the force detected by the fore and aft force transducer-pairs equals torque about the ankle joint. The anterior-posterior projection is obtained by dividing the ankle torque by the total vertical force. This calculation assumes that the upright body can be represented by a simple upright pendulum. Thus, only the effect of movement at the ankle joint is considered, the effect of movements at the knee and hip joints is ignored. A similar calculation employs the signals provided by the lateral pairs of force transducers, on each side of the support platform, to obtain a lateral force projection. The vectorial sum of the anterior-posterior and lateral force projections equals the CFP. As body sway frequencies exceed 0.2 Hz, however, this method for estimating the movement of the body's center of gravity based on CFP becomes increasingly inaccurate, because oscillations of the upper body enter the CFP measurements as inertial reaction forces. Furthermore, if the multi-link nature of the body is ignored, serious errors in understanding a subject's balance disorders can occur.

Investigators have used different types of force platforms to analyze postural sway. Some such force platforms are specifically targeted toward tests for analyzing balance disorders caused by vestibular defects. Quantitative examination of CFP data suggests that subjects having a unilateral vestibular balance deficit, e.g., a balance deficit caused solely by impairment of the vestibular end organs in the inner ear, perform within normal ranges when tests are employed using a fixed force sensitive support surface to perform the balance tests. For this reason, techniques have been introduced which make the control of spontaneous sway by a subject positioned on the CFP measuring support surface more difficult. These techniques make quantification of a vestibular balance disorder easier, by interrupting the non-vestibular sensory inputs that the subject may otherwise use to maintain his balance.

One such technique involves moving the support surface so that it is tilted (forward or backward) in relation to changes in the subject's CFP. This type of controlled platform instability may be obtained using a purely mechanical device, or with a more flexible electronic and computer controlled motor unit. The movement of the support surface platform disrupts the somatosensory inputs which would otherwise be available to the subject. A second technique involves the use of a moveable visual surround, which surrounds the subject, and which is moved to follow the subject's body sway, as estimated by CFP measurement of the subject. This technique disrupts the visual stabilization inputs used by the subject to maintain balance control. By disrupting the somatosensory and visual inputs, a test procedure for analyzing a subject's balance control is able to focus more particularly on the vestibular balance control mechanism. Examples of such test systems and procedures are described in more detail in U.S. Pat. Nos. 4,738,269, 5,052,406 and 5,303,715, issued to Nashner, et al.

Analysis of tests employing these methods of CFP sway quantification have indicated that destabilization of a support surface beneath a subject provides a major diagnostic improvement. However, the diagnostic sensitivity of such methods is still limited, because other variables like trunk rotation and EMG response amplitudes are not taken into account. Furthermore, such methods cannot be used to examine the directional sensitivity (left or right) of a balance disorder, because the movements of the support surface platform are limited to only one axis of rotation (forward and backward). Destabilizing a visual surround by moving it in relation to the CFP provides little additional diagnostic information as far as a vestibular balance deficit is concerned. Furthermore, the destabilization of the visual surround is also limited to forward-backward movements.

Another system that may be used to measure body sway employs light-weight light-emitting sources that are mounted on a subject's body. However, such three-dimensional camera based systems are typically prohibitively expensive for most physical therapy practices specializing in rehabilitation of gait and balance deficits. Moreover, these systems also have a number of technical drawbacks, including excessive computer power requirements, limited on-line capabilities, sensitivity to interfering light sources, and limited range of operation. Thus, although such systems are capable of quantifying gait and other dynamic postural abnormalities, which cannot be achieved using CFP measuring support surfaces, this advantage is outweighed by the price and ease-of-operation advantages of more conventional CFP systems.

A more advanced method for performing non-invasive, sensitive, and reliable tests for the presence of abnormalities in the postural sway of a human subject employs light-weight wearable body sway sensors, such as velocity transducers, that are attached to the upper body of a subject. The body sway sensor output signals are transformed into detailed angular displacement and velocity information by a microprocessor based system processor. The body sway information provided by the body sway sensors is not limited in accuracy by the assumptions used for calculating body sway based on CFP from the signals provided by force transducers embedded in a force plate support surface. The angular position and velocity body sway information derived from the signals provided by the body sway sensors is presented in useful information formats that are displayed to an opera-or on an operator's display unit. The operator's display may provide for comparisons between body sway information obtained from different examination trials or between body sway information obtained from examination trials and body sway information obtained from a normal sample population. The operator's display may also provide an objective measure of the subject's stability. Thus, a physician or physical therapist is able to make an accurate diagnosis of the subject's balance and gait deficits from the body sway information provided on the operator display.

After a balance deficit has been diagnosed and quantified, a physician may prescribe remedial measures to bring the subject's balance control near or within normal limits. The physician may prescribe medication that reduces the action of peripheral senses on the brain. Alteratively, the physician may prescribe a course of physical therapy, which will typically last at least several weeks, with the object of training the subject's brain to deal with a reduced sense of balance when trying to maintain the body upright and prevent a fall. However, neither of these techniques will have an immediate rehabilitation effect on the subject's balance deficit. Moreover, medication can have side effects, and can also reduce the capability of the brain to process balance information from the peripheral senses. A course of physical therapy requires a long training period which may extend over more than two months. These difficulties and limitations associated with conventional remedial measures for dealing with balance deficits are most problematic when the subject is older and likely to have a falling tendency.

Rehabilitation of a subject's balance control deficit may also be accomplished by providing rehabilitory postural feedback to the subject. Such postural feedback may be provided, for example, based upon body sway angle and sway velocity information obtained from body sway sensors, such as velocity transducers, which are attached to the subject's body. The feedback may be in the form of visual, auditory, or tactile stimulation, or may be provided in the form of an electrical signal that is used to directly stimulate the vestibular nerve. A single type of feedback may be used, or different types of feedback may be provided to a subject in combination. A visual feedback system may be incorporated in a pair of light-weight eyewear. An imaging system mounted on the eyewear is used to project a visual feedback display into the eye of the wearer of the eyewear. Auditory feedback may be provided using audio headphones, or a similar device, and frequency modulations around different audible tone center frequencies. Tactile feedback may be provided by vibrators placed on a subject that are used to convey a sense of rotation of the subject's torso. These types of rehabilitory feedback immediately augment the balance signals normally used by the subject's brain to help stabilize body sway and improve balance.

SUMMARY OF THE INVENTION

The present invention provides a method and apparatus for performing non-invasive, sensitive, and reliable tests for the presence of directional specific abnormalities in the balance corrections of human subjects during standing. A method or device in accordance with the present invention may be used as both a diagnostic and a rehabilitory tool for subjects who are prone to abnormal falling in one or more directions, or who wish to improve their balance control in one or more unstable directions.

The present invention is based on the finding that the rotation of a support surface on which a subject is standing elicits a set of biomechanical and muscular responses whose amplitudes can be used to determine whether the subject has a balance deficit which is of vestibular, proprioceptive, central nervous system (CNS), or aphysiologic (non-organic) origin. By rotating the support surface in different directions, it is possible to determine the direction in which the subject's balance deficit manifests itself strongest, as a divergence in response amplitudes from the range expected for that direction in normal subjects. Neither a peripheral vestibular loss nor a loss of proprioceptive function in the lower legs will cause the patient's balance response to be entirely absent.

In accordance with the present invention, the diagnosis and rehabilitation of balance control deficits of a subject is provided by placing the subject in a standing position on a support platform having a moveable support surface. A compact servo-mechanical structure, preferably driven by electrical motors, moves the support surface in any combination of pitch (forward and backward) or roll (left to right) directions. Thus, the subject's stance can be perturbed in a number of directions in order to test for the subject's directional sensitivity to a balance disturbance. Alternatively, the subject's stance can be perturbed in a particular direction either toward or away from the direction of the subject's known greatest balance control instability. Support surface movement is controlled by a system processor, which may be implemented as a microprocessor based system. Displacement angle sensors, which may be implemented using potentiometers provided in the servo-mechanical support surface control structure, are used to provide the angular displacement of the support surface to the system processor. The system processor uses this information to control the support surface angular displacement, and records the support surface angular displacement for use in generating operator and feedback displays for diagnostic and rehabilitory purposes.

In accordance with the presence invention, various types of response measurement devices are used simultaneously to obtain measurements of the subject's response to the movement of the support surface. Force transducers are embedded in the support surface. The signals provided by the force transducers are provided to the system processor, which uses the information provided to calculate the anterior-posterior change in the center of foot pressure (CFP) (or ankle torque if the force transducer information is appropriately scaled) exerted by the subject at each foot when correcting for the support surface movement. Light-weight wearable body sway sensors, such as velocity transducers, are attached to the upper body (e.g., the chest) of the subject. The body sway sensors produce body sway sensor signals which are related to the pitch and roll sway of the subject. The body sway sensor signals are transformed into detailed angular position and velocity information by the system processor. Pairs of electromyographic (EMG) electrodes are placed over the bellies, or fleshy parts, of muscles on the left and right sides of the subject's body, at each of the main body segments, i.e., on the lower leg, trunk, and neck muscles of the subject. The EMG electrodes produce EMG electrode signals in response to the muscular reactions of the subject to the movement of the support surface. The EMG electrode signals are differentially amplified, band pass filtered, rectified, smoothed, digitized, and provided to the system processor to provide a local time envelope of the level of a subject's muscle activity.

The information provided by the force transducers, the body sway sensors, and the EMG electrodes, is provided to the system processor at the same time that the system processor is controlling and recording the profile of the angular displacement of the support surface. The system processor is programmed to transform the various response measures, from the force transducers, body sway sensors, and EMG electrodes, into useful balance correction information formats that are displayed to an operator on an operator's display unit. Displayed information on the subject's balance corrections during an examination trial in which the support surface is moved in one or more directions may include time histories of the subject's trunk sway deviations or angular velocities, EMG recordings, and changes in CFP or ankle torque. The operator's display may also provide for comparisons between different examination trial results obtained from a test subject and for comparisons between the examination trial results obtained from a test subject and examination trial results obtained from a normal sample population.

In accordance with the present invention, the response measure information, obtained from the force transducers, body sway sensors, and EMG electrodes, may be combined, and displayed on the operator display unit in a format which provides an objective measure which may be used for the diagnosis of directional specific abnormalities in the balance corrections of a subject. The present invention may thus preferably provide an automatic diagnosis tool for determining whether a test subject has a vestibular, proprioceptive, CNS lesion, or aphysiologic (simulated) balance disorder, or can be assigned to a normal population. A step-wise discriminant analysis on the various response measures is used to derive weighting factors for each response measure such that an optimal separation between vestibular, proprioceptive, CNS lesion, aphysiologic and normal populations is obtained. These weightings are established using information obtained from subjects known to have vestibular, proprioceptive, CNS lesion, or aphysiologic balance control disorders, or which are known to have normal balance corrections. The same weightings are applied to the response measures obtained from a test subject during an examination trial. The test subject is thus automatically assigned to either a vestibular, proprioceptive, CNS lesion, aphysiologic, or normal population by the present invention. Separate diagnoses may be provided for the left and right sides of the subject for a particular direction of support surface perturbation.

In addition to providing an automatic diagnosis tool, the present invention may display actual values of individual response measures on the operator display unit, along with ranges of normal values for the response measures. The response measures of most interest to the operator may preferably be displayed for all directions in the form of polar plots. Such polar plots may be used by the operator to establish the direction of major pathology of a test subject, and/or to determine if a rehabilitory protocol has had an effect on improving the balance corrections of the test subject.

In accordance with the present invention, the system processor may also be programmed to provide feedback to the subject of the response measures obtained from the force transducers, body sway sensors, and/or EMG electrodes. Feedback may be provided to ensure that the subject is as close as possible to his normal "upright" position prior to the imposition of support surface movement. Once the movement starts, the feedback may be turned off. Alternatively, response measure feedback may be provided to the subject continuously during support surface movement, to provide the subject rehabilitory information on his balance corrections. This feedback information will help the subject stabilize himself quicker in response to balance perturbations caused by the movement of the support surface. Such rehabilitory feedback immediately augments the balance signals normally used by the brain to help stabilize body sway and improve balance.

Feedback may be provided to the subject based on trunk sway angle or angular velocity, deviations of CFP or ankle torque, amplitudes of muscle responses, or a combination thereof. The amount of feedback provided to the subject based on these response measures is determined by the feedback gain. The information provided on the operator's display may be used to compare the subject's balance corrections while being provided feedback with the case where the subject receives no feedback. The information provided on the operator display may thus be used to select the feedback gains which provide an optimal amount of feedback to the subject to improve the subject's balance corrections.

Balance correction feedback of the response measures may be provided to the subject in visual, auditory, or tactile form, or in the form of an electrical signal that is used to stimulate directly the vestibular nerve. A single type of feedback may be used, or different types of feedback may be provided to a subject in combination.

Visual feedback display information may be displayed to a subject on a subject feedback display mounted in front of the subject at eye level. Alternatively, a visual feedback system incorporated in a pair of light-weight eyewear may be used. An imaging system mounted in the eyewear is used to project a visual feedback display generated by the system processor into the eyes of the wearer of the eyewear. Visual feedback may be provided to the subject such that the subject sees a projected image, but the wearer's vision is not otherwise restricted. In this case, the projected image appears to float in the normal visual field of the subject. A subject is thus able to see both the world around him and the feedback display simultaneously. This type of visual feedback display can be used to display visual information to the subject to help him stabilize himself quicker in response to stance perturbations caused by the tilt of the support surface.

Alternatively, the light-weight eyewear may be light excluding, such that the subject sees only the projected feedback image. In this case, a visual scene may be displayed to the subject and moved in such a manner (such as according to the motion of the trunk recorded by body sway sensors) that he is more easily destabilized by the support surface movement. This form of visual feedback can be used for diagnostic purposes, such as for establishing the sensitivity of the subject's balance corrections to visual inputs. Such a destabilizing projected virtual reality image will be far more destabilizing than previously known large, slow moving visual surrounds, because movement of the projected image in response to body motion is nearly instantaneous. By manipulation of the motion of the projected virtual reality image using differing amounts of feedback gain, the ability of the test subject to use visual inputs to control balance in different directions can be explored. Destabilizing visual images can be used to help diagnose balance correction abnormalities in a subject in combination with, or separate from, the moveable support surface of the present invention.

For visual rehabilitory feedback, the visual feedback display preferably includes a horizontal bar that moves in relation to the forward and backward (pitch) and left and right (roll) sway of the subject's upper body. The width of the horizontal bar increases or decreases in relation to the vectorial combination of the roll and pitch velocities of the subject's upper body. The sensitivity of the movement and width of the horizontal bar to the sway angle and sway velocity of the subject are visual feedback gain parameters which may be adjusted by the operator to help improve the subject's balance control.

A subject provided with visual feedback can be tested to obtain response measures in accordance with the present invention under eyes open or eyes closed conditions, or with possibly destabilizing visual feedback. Such tests may be used to provide information on the possible efficacy of stabilizing visual feedback in improving the subject's balance control.

For auditory feedback, response measure information, such as information on the roll and pitch displacements of the subject's trunk, are presented to the subject aurally. Auditory feedback information can be presented to the subject prior to the onset of the support surface tilt, to help the subject maintain an upright position, and turned off once the support surface movement has started. Alternatively, auditory feedback may be provided to the subject continuously during the movement of the support surface, to help the subject improve his balance corrections during an examination trial. Roll and pitch angular displacement of the subject may be provided in the form of auditory feedback as frequency modulations around two different audible tone center frequencies, e.g., 500 Hz and 1500 Hz. The velocity of angular sway may be presented as an increased or decreased tone volume. The depth of frequency modulation and volume of the auditory signals are auditory feedback gain parameters which may be set by the operator to help improve the subject's balance corrections in one or more directions.

Tactile feedback may be provided by vibrators that are placed on the subject to convey a sense of rotation of the subject's torso. For example, two vibrators placed on the subject may be used to convey a sense of forward and backward sway by modulation of the frequency of vibration with respect to the measured sway velocity, and by varying the amplitude of vibration with respect to the sway angle.

Response measure feedback signals may also be provided as varying electrical signals which are used to directly stimulate the vestibular nerve. Such stimulation is sensed by the subject as a change in the angular and/or linear position of the head. Feedback signals for such direct electrical stimulation are transmitted transcutaneously to an implantable device directly connected via electrodes to the close proximity of the vestibular nerve or to the nerve itself. The pulse rate, amplitude, and duty cycle of the electrical stimulation signal at the electrodes is varied with respect to selected response measures, such as the sway angle and angular velocities that are determined by the system processor based on the signals provided by body sway sensors attached to the subject's upper body.

Further objects, features, and advantages of the present invention will be apparent from the following detailed description taken in conjunction with the accompanying drawings.

DETAILED DESCRIPTION OF THE INVENTION

Figure 1:
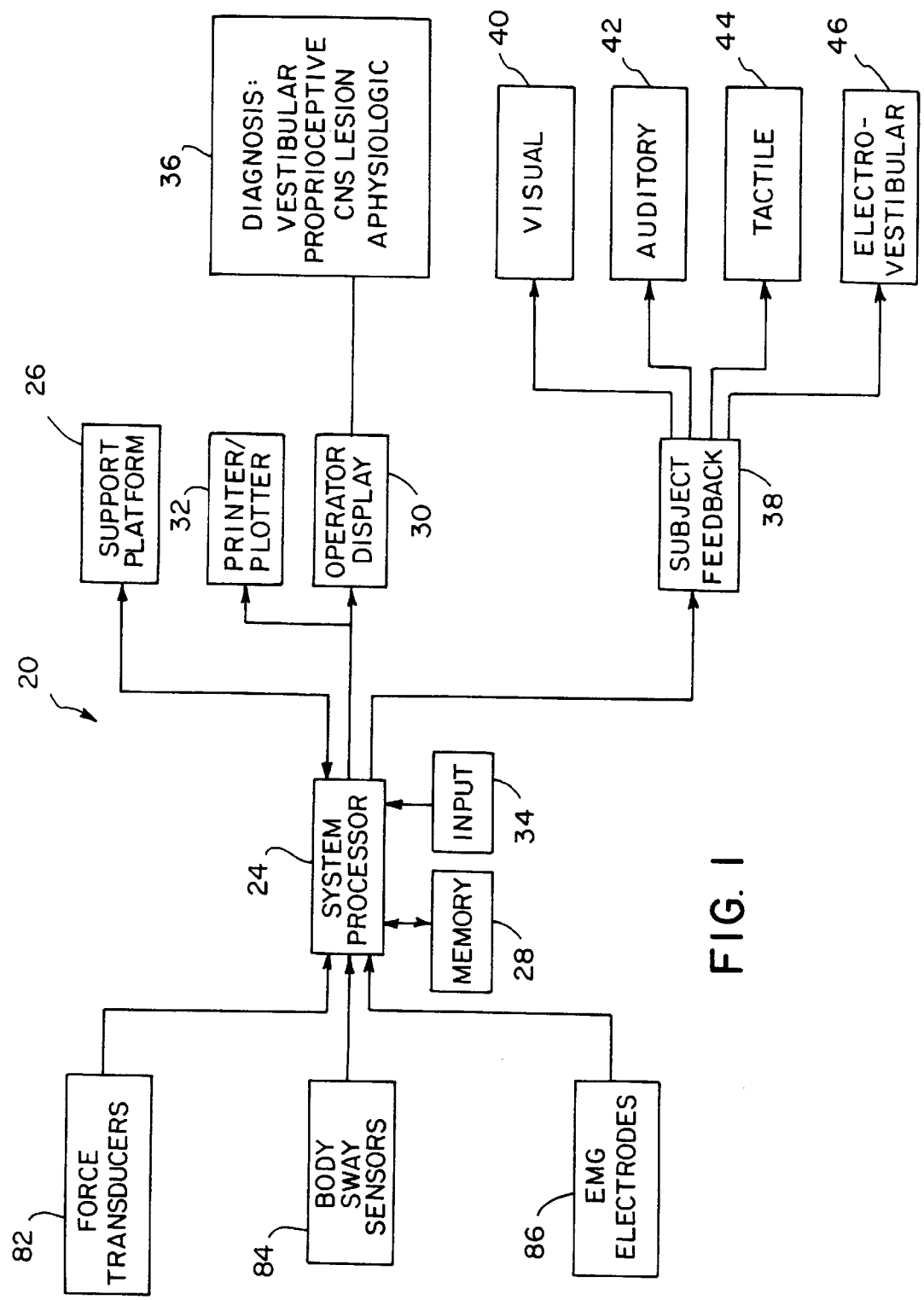
FIG. 1 is a schematic block diagram of a balance disorder diagnosis and rehabilitation system in accordance with the present invention.

A balance disorder diagnosis and rehabilitation system in accordance with the present invention is illustrated generally, in block diagram form, at 20 in FIG. 1. A schematic illustration of a test subject 22 in standing position on an exemplary embodiment of a balance disorder diagnosis and rehabilitation system 20 in accordance with the present invention is provided in FIG. 2. The balance disorder diagnosis and rehabilitation system 20 is controlled by a system processor 24. The system processor 24 provides control signals to control a support platform 26 to perturb the stance of the subject 22 in any combination of pitch (forward and backward) and/or roll (left to right) directions. The system processor 24 receives signals from various response measurement devices which indicate the subject's balance correction response to the stance perturbations. As will be discussed in more detail below, these response measures are employed by the system processor 24 to generate an operator display whereby abnormalities in the balance corrections of the subject 22 may be diagnosed. As also will be discussed in more detail below, the system processor 24 may also employ the response measures to provide balance correction feedback to the subject 22 to help the subject improve his response to the stance perturbations elicited by the support platform 26.

The system processor 24 may be implemented as a conventional microprocessor based computer system having computer memory 28, an operator's display unit 30, e.g., a standard 14-inch computer display console, a printer or plotter 32, and an operator's input device 34, such as a conventional computer keyboard. The processor memory 28 may include short-term memory, e.g., RAM, as well as long-term memory, such as is provided by a conventional magnetic disk storage system. The system processor's memory 28 operates in a conventional manner to store the programmed series of instructions and algorithms that control operation of the system processor 24 and to store data generated by the system processor 24.

In accordance with the present invention, the system processor 24 is programmed to control the support platform 26 to perturb the stance of a subject 22 standing on the support platform 26 in either a pitch or roll direction, or a combination thereof. In accordance with the present invention, the system processor 24 is also programmed to transform response measure signals, obtained during an examination trial wherein the support platform 26 is controlled to perturb the stance of the subject 22, into useful balance correction information formats. The balance correction information is displayed by the system processor 24 in the form of an operator's display that is presented to the operator on the operator's display unit 30. From this formatted information, the system operator, e.g., a physician, is able to analyze the balance corrections of the subject during the stance perturbations elicited by the support platform 26, to thereby diagnose the existence, cause (i.e. vestibular, proprioceptive, CNS lesion, or aphysiologic), and side of any abnormality in the balance corrections of the subject 22. A hard copy of the balance correction information provided on the operator's display unit 30 may be obtained using the system printer or plotter 32.

In accordance with the present invention, the system processor 24 may also be programmed to provide feedback 38 of the balance correction information to the subject 22. As will be discussed in more detail below, the balance correction feedback 38 may be provided to a subject in visual, auditory, or tactile form, or may be provided in the form of a varying electrical signal for directly stimulating the vestibular nerve. Visual 40, auditory 42, tactile 44, and electro-vestibular 46 feedback systems may, therefore, be provided in accordance with the present invention to deliver balance correction feedback signals provided by the system processor 24 to the subject 22. It should be understood that a single type of feedback, i.e., visual, auditory, tactile, or electro-vestibular, or a combination of feedback types, may be provided to a subject at any one time. Thus, a balance disorder diagnosis and rehabilitation system 20 in accordance with the present invention need not include every feedback system 40, 42, 44, and 46 illustrated in FIG. 1, but may include any one of the feedback systems, or any combination of multiple feedback systems.

Figure 3:
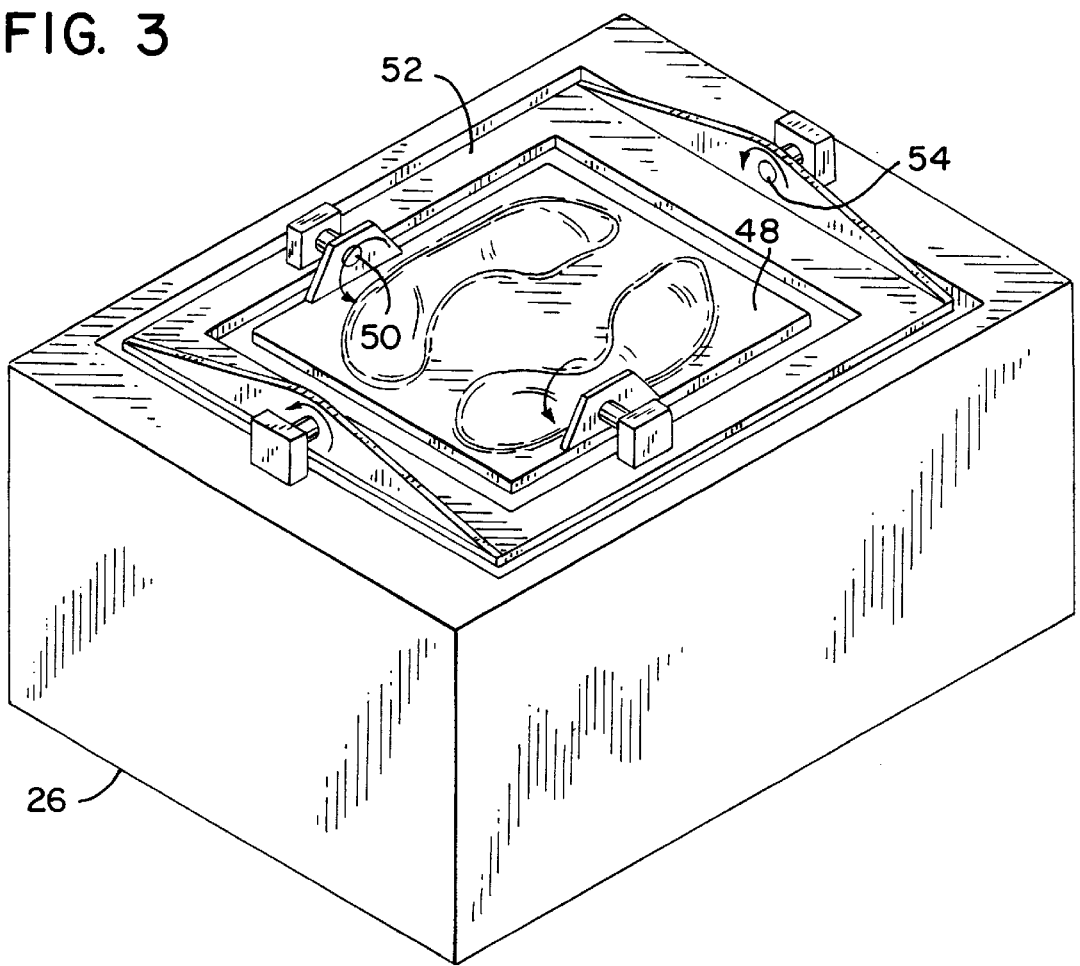
FIG. 3 is a perspective view of a support platform including a support surface for perturbing a subject's stance in any combination of roll and pitch directions in accordance with the present invention.

An exemplary embodiment of a support platform 26 in accordance with the present invention is described and illustrated with reference to FIG. 3. The support platform 26 includes a pitch direction support surface 48 which is controlled to rotate about pivot points 50 in the pitch (forward and backward) direction. The pitch direction support surface 48 is adapted such that the subject 22 may stand on the top of the support surface 48. The axis of rotation of the pitch direction support surface 48 is fixed at the average height of the ankles above the lower surface of the feet of normal subjects. The subject 22 is asked to stand on the support surface 48 so that the direction of this axis is aligned with the imaginary line running through the center of rotation of both ankle joints. Movement of the pitch direction support surface 48 in the pitch direction will cause a forward or backward perturbation in the stance of a subject 22 standing on the support surface 48.

The pitch direction support surface 48 is, itself, mounted on a roll direction support surface 52. The roll direction support surface 52, which is mounted on the support platform 26 itself, is controlled to rotate about pivot points 54 in the roll (left to right) direction. The axis of rotation of the roll direction support surface 52 is perpendicular to the axis of rotation of the pitch direction support surface 48 in the same horizontal plane. Thus, the axis of rotation of the roll direction support surface 52 runs fore to aft centered between the subject's feet when a subject 22 is standing in a proper position on the support platform 26.

It is apparent that by controlling the pitch direction support surface 48 to tilt in the pitch direction, while simultaneously controlling the roll direction support surface 52 to tilt in the roll direction, the stance of a subject 22 standing on the support platform 26 may be perturbed in any direction. Preferably, the pitch direction 48 and roll direction 52 support surfaces are designed to tilt at least 8° in either direction. It is apparent that a support platform wherein the roll direction support surface is mounted on the pitch direction support surface may also be used to perturb the subject's stance in any combination of pitch and roll directions.

Figure 4:
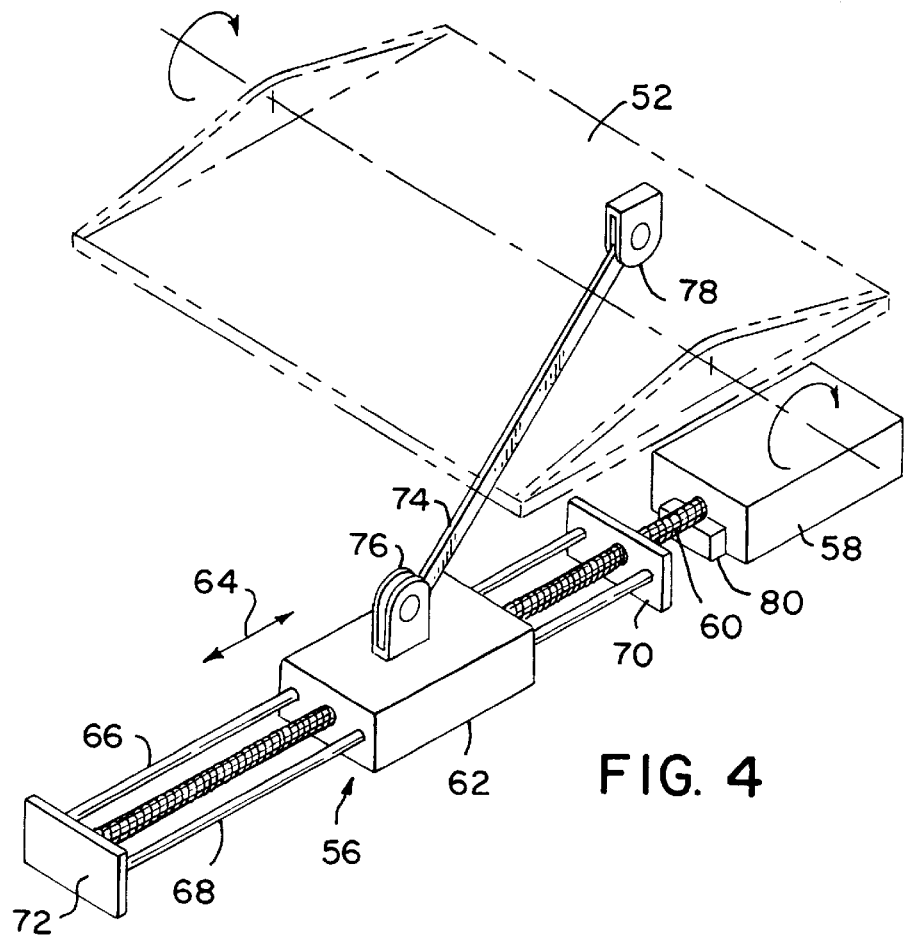
FIG. 4 is a perspective view of a servo-mechanical structure for tilting the support surface of the support platform of FIG. 3 in one direction.
Figure 5:
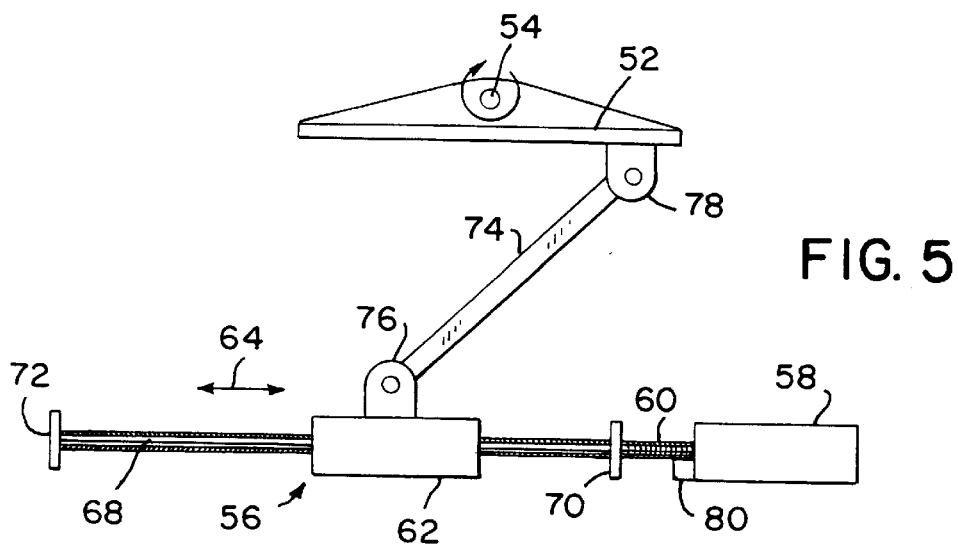
FIG. 5 is a side view of the servo-mechanical structure of FIG. 4.

An exemplary and preferred compact servo-mechanical structure 56 for controlling the rotational position of the roll direction support surface 52 about the rotational axis 54 is illustrated in and described with reference to FIGS. 4 and 5. The servo-mechanical support surface control structure 56 includes a rotating electric motor 58 which drives a lead screw 60. The threads of the lead screw 60 are engaged with a translational motion box structure 62. When the rotating electrical motor 58 is operated to turn the lead screw 60, the translational motion box structure 62 is moved back and forth, in the direction indicated by arrows 64, along the lead screw 60 and a track formed by support rods 66 and 68. The support rods 66 and 68 support the translational motion box structure 62 and prevent any rotational motion thereof. End stops 70 and 72 limit the amount of translational motion of the translational motion box structure 62 along the lead screw 60 and the support rods 66 and 68. A bar 74 is connected at one end by a hinge structure 76 to the translational motion box structure 62, and at the other end by a hinge structure 78 to the under side of the roll direction support surface 52. As the translational motion box structure 62 is moved along the lead screw 60 and support rods 66 and 68, the bar 74 either pushes or pulls on the under side of the support surface 52, to thereby rotate the support surface 52 about the rotational axis 54. Preferably, the servo-mechanical support surface control structure 56 is capable of rotating the support surface 52 about the rotational axis 54 by at least approximately 8 degrees in either direction. A similar servo-mechanical support surface control structure is used to rotate the pitch direction support surface 48 about the rotational axis 50. It should be clear that, in order to achieve perturbation of a subject's stance in any combination of pitch and roll directions, the servo-mechanical support surface control structure that controls the pitch direction support surface 48 must be mounted, along with the support surface 48 itself, so as to move with the roll direction support surface 52. It should also be apparent that other systems may be used to control the rotational position of the pitch direction 48 and roll direction 52 support surfaces. For example, the rotational positions of the support surfaces can be controlled by a system consisting of an electric motor, a fixed displacement hydraulic pump, and a hydraulic cylinder.

A device for measuring the angular displacement of the support surfaces 48 and 52 in the pitch and roll directions may preferably be incorporated in the servo-mechanical support surface control structures 48 and 52. For example, a potentiometer 80 may preferably be mounted on the servo-mechanical support surface control structure 56 so as to engage the lead screw 60. As the lead screw 60 is rotated by the electric motor 58 to rotate the support surface 52 about the rotational axis 54, the potential value of the potentiometer 80 is varied. The potential of the potentiometer 80 is, therefore, relative to the angular displacement of the support surface 52. The potential of the potentiometer 80 may be monitored by the system processor 24 to determine, in a conventional manner, the angular displacement of the support surface 52 in the roll direction. A similarly placed potentiometer in the servo-mechanical support surface control structure for the pitch direction support surface 48 may be used to provide a signal to the system processor 24 from which the angular displacement of the pitch direction support surface 48 in the pitch direction can be determined. The measured angular displacement of the support surfaces 48 and 52 in the pitch and roll directions, respectively, are used by the system processor 24 to control the angular displacement of the support surfaces 48 and 52 and, as will be described in more detail below, may be displayed to the system operator as part of the balance correction information operator display provided to the operator on the operator display unit 30.

In accordance with the present invention, the system processor 24 receives balance correction response measurements from three response measurement sources. Force transducers 82, embedded in the pitch direction support surface 48, are used to provide signals from which the change in the center of foot pressure (CFP) (or ankle torque if the force transducer information as appropriately scaled) exerted by the subject 22 at each foot when correcting for support surface movement can be calculated. Light-weight wearable body sway sensors 84, such as velocity transducers, are attached to the upper torso of the subject 22 in such a way as to measure the pitch and roll sway of the subject 22. Muscular reactions to the movement of the support surface are recorded with pairs of electromyographic (EMG) electrodes 86 placed over muscle bellies on the left and right sides of the subject's body at each of the main body segments.

The force transducers 82 may be embedded in the four corners of the pitch direction support surface 48, or, alternatively, may be embedded in two separate support surface plates (not shown) mounted in the pitch direction support surface 48 under each foot of the subject 22. CFP, or ankle torque, may be computed from the signals provided by the force transducers 82 in a conventional manner. The force transducer outputs are employed to obtain a projection, on the support surface platform, of the resultant forces acting at the subject's center of gravity. An anterior-posterior, front-to-back, projection is obtained by assuming that the difference between the force detected by the fore and aft force transducer-pairs equals torque about the ankle joint. The anterior-posterior projection is obtained by dividing the ankle torque by the total vertical force. This calculation assumes that the upright body can be represented by a simple upright pendulum. Thus, only the effect of movement at the ankle joints is considered, the effect of movements at the knee and hip joints is ignored. A similar calculation employs the signals provided by the lateral pairs of force transducers, on each side of the support platform, to obtain a lateral force projection. The vectorial sum of the anterior-posterior and lateral force projections equals the CFP. Conventional methods and devices for obtaining the force transducer signals and deriving the CFP or ankle torque from the force transducer signals may be employed in the present invention. If separate support surface plates with force transducers 82 mounted therein are provided under each foot of the test subject 22 a separate measure of CFP or ankle torque can be obtained for each leg.

The body sway sensors 84 are preferably attached to the upper body, e.g., the chest, of the subject 22 to thereby register at least the roll and pitch motion of the subject's upper body. The location of the body sway sensors 84 on the subject's body is determined by the axis of sensitivity of the sensors. A sensor mounted on the front or back of the subject's chest may be used to register roll angular deviations of the patient's trunk from the vertical, and roll angular velocities. A second sensor mounted on the side of the subject's chest may be used to register pitch angular deviations from the vertical, and pitch angular velocities. The sensors 84 may preferably be secured to the chest of the subject 22 by placing the sensors 84 in tight fitting pouches attached to elasticated straps 88 which hold the sensors 84 tightly against the subject's chest. It should be apparent, however, that other conventional means may also be used to attach the sensors 84 to the subject 22, either over or under the subject's clothing. If desired, other sensors, not shown, may also be attached to the subject's chest. For example, a third sensor may be used, if desired, to register yaw, i.e., turning about the vertical axis, angular deviations, and yaw angular velocities. Similarly, the subject 22 may wear additional sensors at other bodily locations, such as at the waist, upper leg, or lower leg. These additional sensors may be used to provide information on the roll and pitch amplitudes and velocities at these body locations, in addition to the body sway angle and angular velocities of the subject's trunk. If such additional sensors are used, the present invention may be employed as a complete body motion analysis system. The system processor 24 may be programmed to analyze and display all available body motion information. Moreover, the body motion information provided by the sensors at body locations other than the trunk can be used by the system processor 24 to infer trunk sway angles and angular velocities.

Various different types of sensors 84 may be used to measure the body sway angle and body sway angular velocity of the subject 22. Preferably, the type of sensor that is used is capable of providing a direct measurement of angular velocity, i.e., an angular velocity sensor, and is substantially insensitive to the gravity vector and to linear accelerations, i.e., straight up and down, backward and forward, and side-to-side motions of the subject's entire body. An exemplary and preferred body sway sensor is the Litef Micro Fors 36 Fiber Optic Rate Sensor, made by Litef GmbH of Freiburg, Germany, D-79007. This preferred sensor is an angular velocity sensor that may be programmed to provide either angular deviation or angular velocity information in digital form, at a selected scale factor, to the system processor 24, which stores and transforms the digital angular deviation or velocity values into an information format which is provided to the system operator. For this angular velocity sensor, the angular velocity scale factor is relative to a maximum sensed rate of 327° per second.

Body sway sensors which measure Coriolis forces in vibrating structures to sense angular velocities may also be used. Such a sensor is, for example, available as part number ADS-C232 from Watson Industries Inc. of Eau Claire, Wis., U.S.A. This exemplary product has a scale factor of 30° per second per volt. Similar products are also available. This type of sensor is, however, not preferred, because such sensors generally provide an analog output, requiring the use of an analog-to-digital converter, to be placed between the sensor 84 and the digital system processor 24, in order for the sensor signals to be processed digitally by the system processor 24. Acceptable forms of this type of sensor device may, however, become available in the future. An acceptable device would, for example, be a miniaturized version of the system produced by Watson Industries, or its equivalent, with the capability of providing direct digital outputs over a serial line interface to a computer, such as the system processor 24.

The body sway sensors 84 may also be implemented using pairs of linear acceleration transducers (accelerometers) set at fixed distances from one another on the subject's body. Such devices may be used to measure angular accelerations, which may then be transformed into angular velocity and angular deviation values by suitable analog or digital integration algorithms implemented, for example, in the system processor 24. However, it is noted that most linear accelerometers have inherent drift problems. Thus, the use of linear accelerometers to provide body sway sensing is not preferred, unless the drift problems currently inherent in most linear accelerometers are reduced.

Whatever type of body sway sensors 84 are used, it should be clear that it is not crucial that the sensor inputs to the system processor 24 be angular velocity signals, although this is preferred. If angular displacement signals are provided to the processor 24, these may be differentiated to obtain angular velocity. If angular acceleration signals are provided by the sensors 84, these may be integrated by the system processor 24 to obtain angular velocity and displacement. Standard digital differentiation and integration algorithms may be used by the system processor 24 to perform the differentiation and integration functions, as necessary.

The subject's muscular responses to the movement of the support surfaces 48 and 52 are recorded using pairs of EMG electrodes 86 placed over muscle bellies on the left and right sides of the subject's body at each of the main body segments of interest. EMG electrodes 86 may preferably be placed on the lower leg, trunk, and neck muscles of the subject 22. Exact placement of the EMG electrodes will depend on the muscular responses which are to be measured. Preferably, EMG electrodes 86 are placed on the subject 22 to record the responses of the subject's quadriceps, soleus, tibialis anterior, trapezius, paraspinalis, and gastrocnemius. More, fewer, or different muscle responses may also be measured in accordance with the present invention. The EMG electrodes 86 are preferably placed on the subject 22 to sense the muscular reactions on both the left and right sides of the subject's body. Conventional EMG electrodes may be used. The signals from the EMG electrodes are differentially amplified, band pass filtered, rectified, smoothed, and digitized, in a conventional manner, to provide a local time envelope of the level of muscle activity to the system processor 24. The amplification, filtering, rectification, smoothing, and digitization of the EMG electrode signals may be performed in a conventional manner, using conventional analog and/or digital circuitry, and may be performed, in whole or in part, by the system processor 24, itself.

A balance disorder diagnosis and rehabilitation system 20 in accordance with the present invention may be used to diagnose abnormalities in the balance corrections of a subject 22. The balance disorder diagnosis and rehabilitation system 20 of the present invention may be used to determine whether a subject has a balance correction abnormality, whether the abnormality is of a vestibular, proprioceptive, CNS lesion, or aphysiologic origin, and the side or direction of the subject's greatest balance instability. In accordance with the present invention, such a diagnosis is performed by placing a subject 22 in a standing position on the support platform 26. Body sway sensors 84 and EMG electrodes 86 are placed on the subject 22 in the manner described previously. The system processor 24 then provides control signals to the support platform 26 to tilt the support surfaces 48 and/or 52 in one or more directions. The movement of the support surfaces perturbs the subject's stance in the combined direction of tilt of the support surfaces 48 and 52.

The support surfaces 48 and 52 may be moved in a number of different directions in order to test for a subject's directional sensitivity to a balance disturbance. Alternatively, the support surfaces 48 and 52 may be tilted in a direction so as to perturb the subject's stance in a direction toward or away from the direction of the subject's known greatest balance correction instability. Various different test protocols may be employed. For example, the same support surface angular displacement may be employed with the subject's eyes open, and then with the subject's eyes closed, to observe the subject's response measures when visual inputs are available to the subject (eyes open) and when visual inputs are not available to the subject (eyes closed). The test protocol may also involve presenting the subject with a virtual reality visual display using a pair of light excluding eyewear (to be described in more detail below). The virtual reality scene may be made to move in the same direction, by the same amount, and at the same velocity, as the trunk movements of the subject, thereby testing the subject's response measures when visual inputs are stabilized with respect to the subject.

At the same time that the system processor 24 is controlling the support platform 26 to perturb the subject's stance in one or more pitch or roll directions, signals from the force transducers 82 in the support platform 26, from the body sway sensors 84 attached to the subject's torso, from the EMG electrodes 86, and from the potentiometers 80 recording the angular displacements of the support surfaces 48 and 52 in the roll and pitch directions, are provided to the system processor 24. The system processor 24 is programmed to transform the response measurements from the force transducers 82, body sway sensors 84, and the EMG electrodes 86, into useful information formats that are displayed to an operator on the operator's display unit 30. Quantified information on the subject's balance corrections may include time histories of, for example, the subject's trunk sway deviations or angular velocities, the EMG signal recordings, and changes in CFP or ankle torque, in response to angular displacement of the support surfaces. The operator's display may also provide comparisons between different examination trial results for the test subject and between examination trial results from a test subject and examination trial results from a normal sample population.

Figure 6:
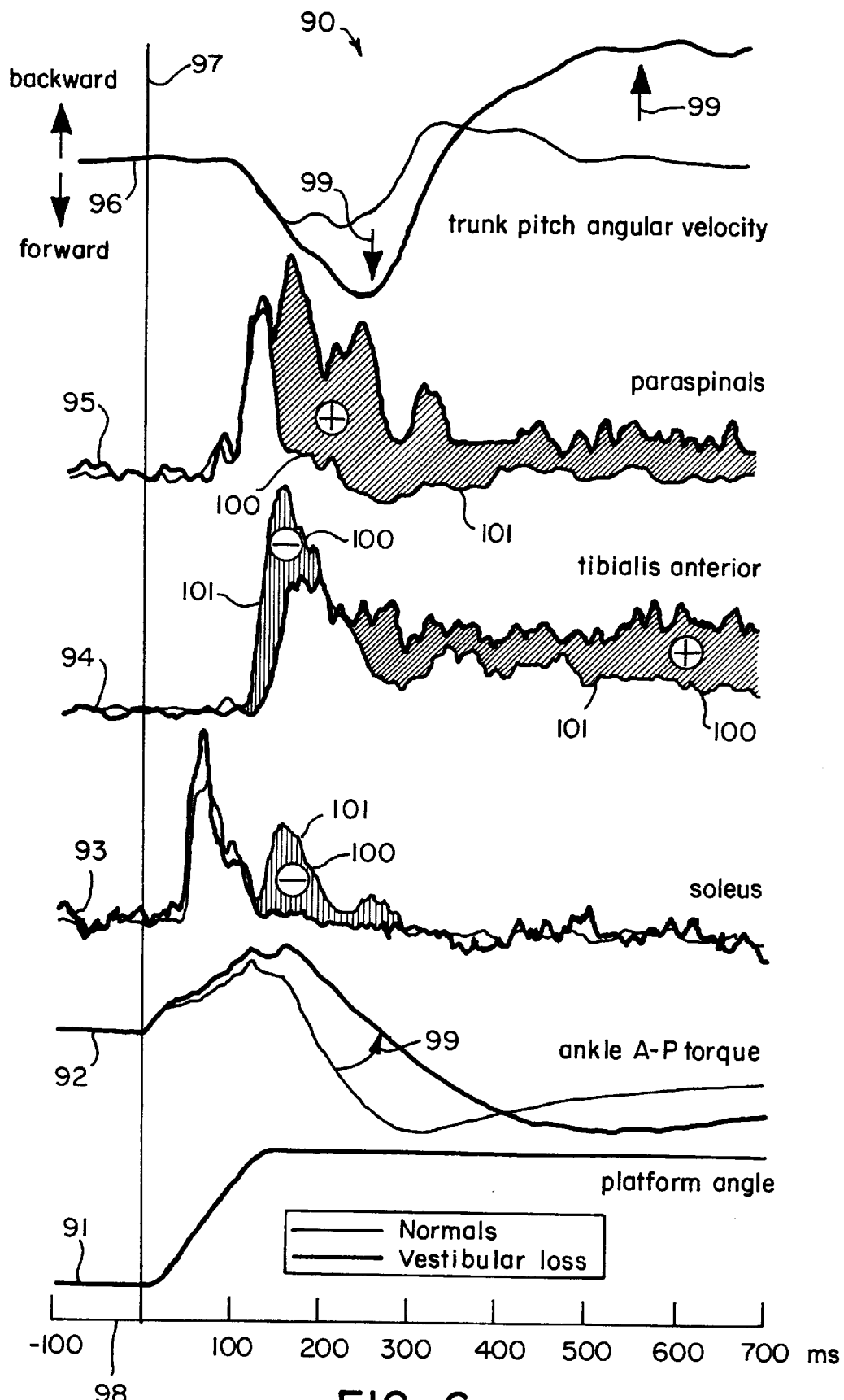
FIG. 6 is an illustration of an exemplary operator's display in accordance with the present invention, providing information derived from various response measures obtained during a pitch toe-up examination trial of a test subject having a peripheral vestibular deficit.

Exemplary operator displays in accordance with the present invention, showing response measures obtained from examination trials performed on a test subject and from those performed on a normal sample population, are shown in FIGS. 6–11. FIG. 6 illustrates an exemplary operator display 90 showing examination trial results for a test subject having a balance correction abnormality caused by a peripheral vestibular deficit. These results were obtained by rotating the support surface backward, i.e., pitch toe-up. The exemplary operator display 90 includes six time history graphs including various response measures for the examination trial period of 1 second. In each graph the thick solid line represents the particular response measure for the subject during an examination trial performed with the subject's eyes closed (or eyes open, or with a stabilized virtual reality scene provided to the test subject, depending on the test protocol desired). The thin solid line represents the selected response measure for a normal population during an examination trial under the same visual condition protocol. The time histories provided in the exemplary user display 90 include time histories of the following response measures over the examination trial period: the angular rotation 91 of the support surface (in degrees of, in this case, pitch), the ankle torque 92 (in Nm, derived from signals provided by the force transducers in the support surface 26); the subject's soleus 93, tibialis anterior 94, and paraspinal 95 responses (each in millivolts, derived from the signals provided by pairs of EMG electrodes 86 placed on the subject 22); and trunk angular velocity 96 (in degrees per second of, in this case, pitch, derived from the signals provided by the body sway sensors 84 placed on the trunk of the subject 22). Anterior-posterior ankle torque 92, and soleus 93, tibialis anterior 94, and paraspinal 95 responses for the right side of the body are presented in the operator display 90. Lateral ankle torque, left side muscle responses, trunk roll angular velocity, and platform roll angle for the test period, along with other information, could also be displayed as a part of the operator display 90, or as part of another operator display. The operator display 90 also includes a zero latency line 97, derived from the first inflexion of the support surface angular velocity, and a time line 98 extending from time 0 at the latency line 97.

The operator display 90 allows the system operator, e.g., a physician, to compare the response measures obtained from the examination trial of a test subject with the examination trial results obtained from a normal sample population under the same visual protocol conditions. In particular, to make a diagnosis, an operator may consider the following information provided in the operator display 90: the differences in the changes in ankle torque between the test subject and those of the normal population between 160 and 260 ms after the support surface moves with respect to zero latency 97, differences in the areas between the test subject's EMG responses and those of the normal population between the intervals 40–100 ms, 80–120 ms, 120–220 ms, 240–340 ms, and 350–700 ms after zero latency 97, and increases in the trunk angular velocity from that of the normal population. Large differences between the response measures obtained from examination trials of a test subject and response measures obtained from a normal sample population may be automatically highlighted by markers displayed on the operator display 90 along with the response measure time histories. For example, arrows 99 may be used to indicate clearly large differences in ankle torque and angular velocity between examination trial results obtained from a normal population and the examination trial results obtained from the test subject. Plus or minus signs 100 may be displayed on the operator display 90 to indicate clearly large differences in EMG responses obtained from a normal sample population and those obtained from the examination trial of the test subject. Large areas of difference between the EMG responses obtained from the normal sample population and from the examination trial of the test subject may also be shaded or highlighted 101, using a different color or pattern to indicate positive or negative deviations of the EMG responses obtained from the examination trial of a test subject from the examination trial results obtained from a normal sample population. By using response measure comparison information from multiple response measure sources, as presented in a highly readable form on the operator display 90, an operator, e.g., a physician, is able to make a rapid and accurate diagnosis of the presence or absence of a balance-correction abnormality. For the exemplary operator display 90 illustrated in FIG. 6, the pattern of changes in the displayed response measures between the examination trial results obtained from the test subject compared to those of the normal population indicate that the test subject has a balance correction abnormality caused by a peripheral vestibular deficit.

Figure 7:
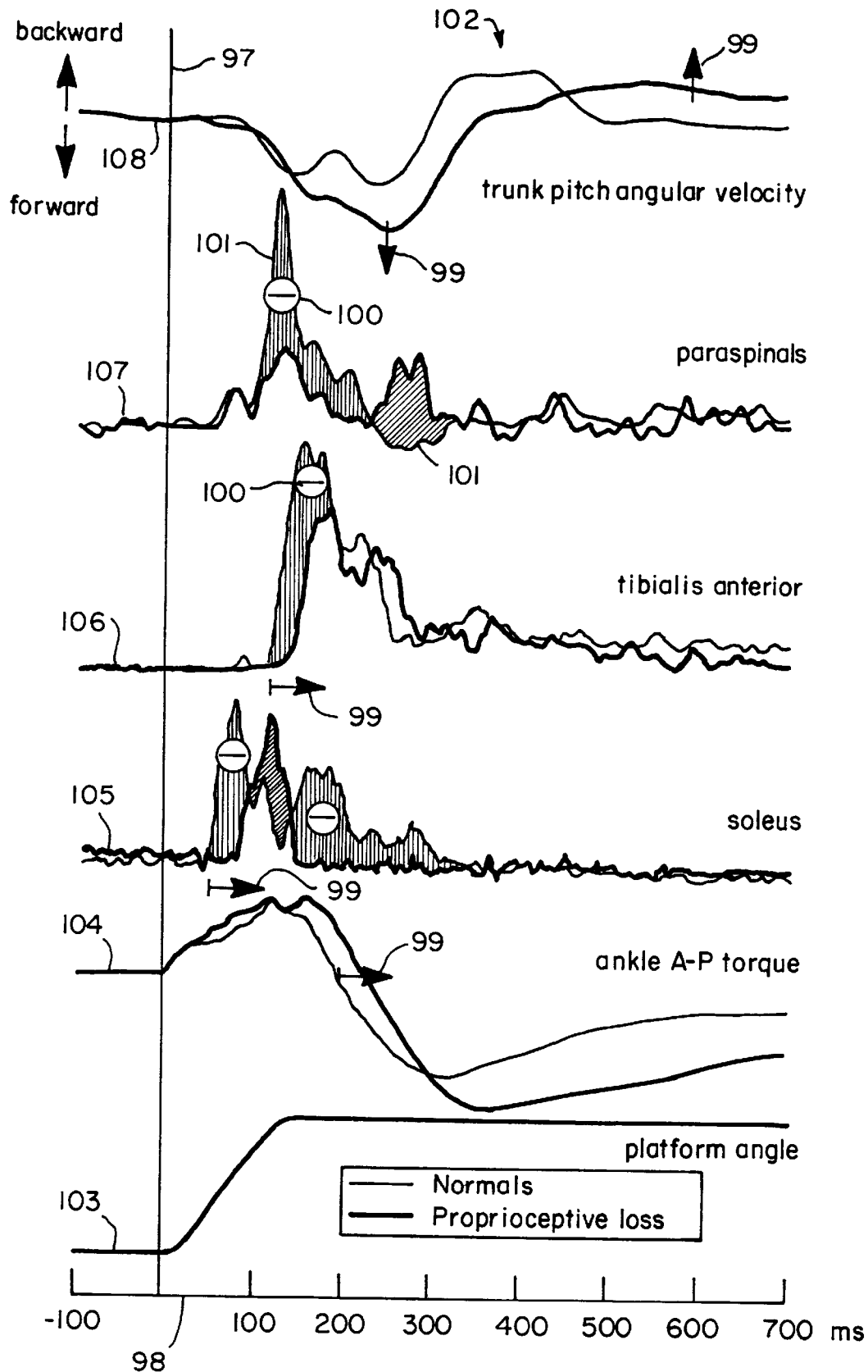
FIG. 7 is an illustration of an exemplary operator's display in accordance with the present invention, providing information derived from various response measures obtained during a pitch toe-up examination trial of a test subject having a proprioceptive deficit of the lower legs.

Another exemplary operator display 102 in accordance with the present invention is illustrated in FIG. 7. This exemplary operator display 102 shows the examination trial results for a test subject having a balance correction abnormality caused by a lower-leg proprioceptive loss. These results were also obtained by rotating the support surface backward, i.e., pitch toe-up. The exemplary operator display 102 includes six time history graphs including various response measures for the examination trial period of 1 second. In each graph, the thick solid line represents the particular response measure for the subject during an examination trial performed with the subject's eyes closed (or eyes open, or with a stabilized virtual reality scene provided to the test subject, depending on the test protocol desired). The thin solid line represents the selected response measure for a normal population during an examination trial under the same visual condition protocol. The time histories provided in the exemplary operator display 102 include time histories of the following response measures over the examination trial period: the angular rotation 103 of the support surface (in degrees of, in this case, pitch); the ankle torque 104 (in Nm, derived from signals provided by the force transducers in the support surface 26); the subject's soleus 105, tibialis anterior 106, and paraspinal 107 responses (each in millivolts, derived from the signals provided by pairs of EMG electrodes 86 placed on the subject 22); and trunk angular velocity 108 (in degrees per second of, in this case, pitch, derived from the signals provided by the body sway sensors 84 placed on the trunk of the subject 22). Anterior-posterior ankle torque 104, and soleus 105, tibialis anterior 106, and paraspinal 107 responses for the right side of the body are presented in the operator display 102. Lateral ankle torque, left side muscle responses, trunk roll angular velocity, and platform roll angle for the test period, along with other information, could also be displayed as a part of the operator display 102, or as a part of another operator display. The operator display 90 also includes the zero latency line 97, derived from the first inflexion of the support surface angular velocity, and a time line 98 extending from time 0 at the latency line 97.

The exemplary operator display 102 allows a system operator, e.g., a physician, to compare response measures obtained from the examination trial of a test subject with the examination trial results obtained from a normal sample population under the same visual protocol conditions. In particular, to make a diagnosis, an operator may consider the following information provided on the operator display 102: the differences in the changes in ankle torque between the test subject and those of the normal population between 160 and 260 ms after the support surface moves with respect to zero latency 97, differences in the areas between the test subject's EMG responses and those of the normal population between the intervals 40–100 ms, 80–120 ms, 120–220 ms, 240–340 ms, and 350–700 ms; and increases in trunk angular velocity from the normal response. As discussed previously, large differences between the response measures obtained from the examination trial of the test subject and the examination trial results obtained from a normal sample population are preferably automatically marked on the operator display 102, using, e.g., arrows 99, plus or minus signs 100, and/or shading or highlighting 101, to indicate clearly such differences. Response measure information obtained from a variety of sources is presented to an operator in a highly readable operator display format 102. This allows the operator, e.g., a physician, to make a quick and accurate diagnosis of the presence or absence of a balance-correction abnormality. For the exemplary operator display 102 illustrated in FIG. 7, the changes in response measures between the examination trial results obtained from the test subject compared to those of the normal population indicate that the test subject has a balance correction abnormality caused by a lower-leg proprioceptive loss.

Figure 8:
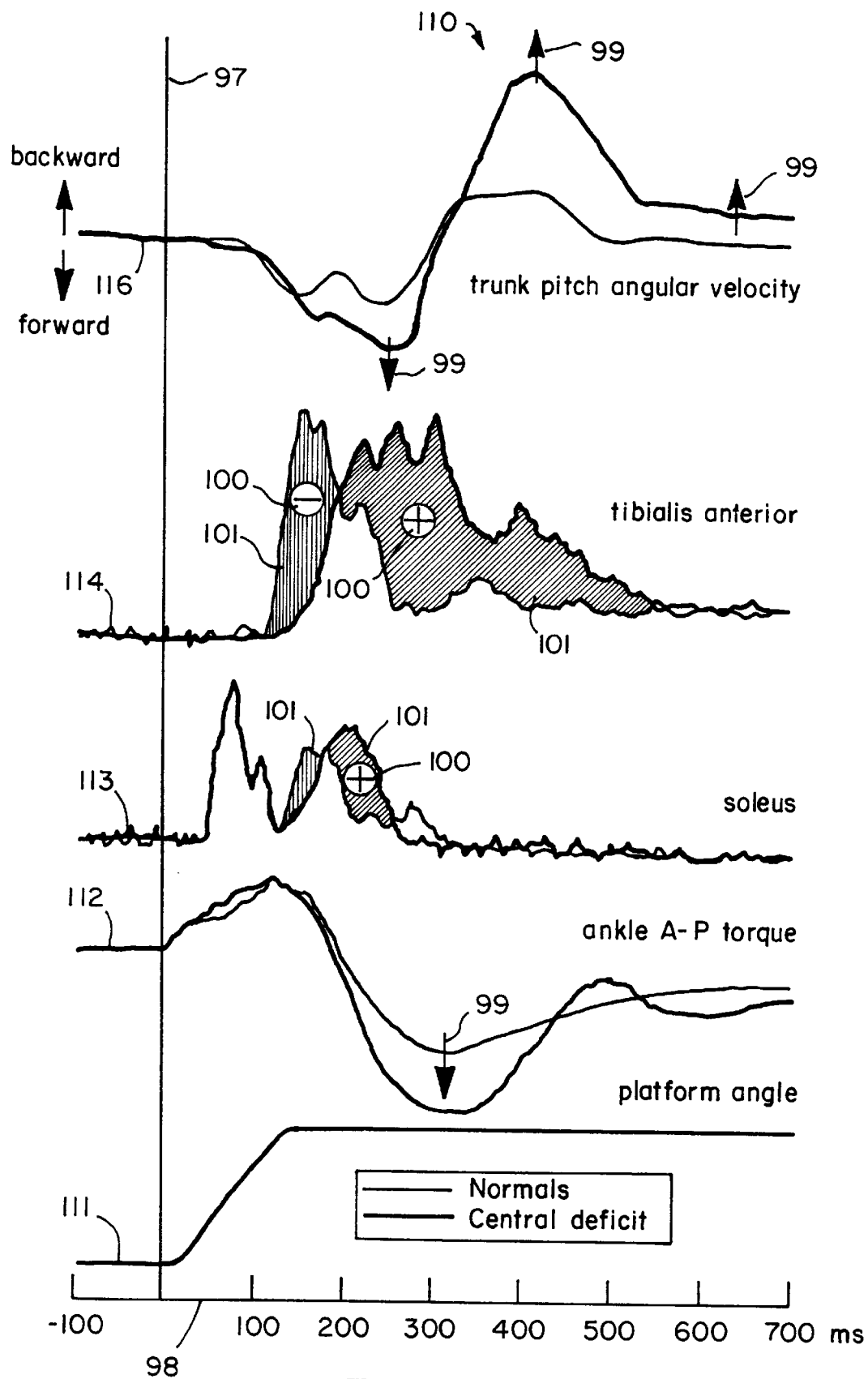
FIG. 8 is an illustration of an exemplary operator's display in accordance with the present invention, providing information derived from various response measures obtained during a pitch toe-up examination trial of a test subject having a central nervous system (CNS) deficit.

Yet another exemplary operator display 110 in accordance with the present invention is illustrated in FIG. 8. This exemplary operator display 110 shows examination trial results for a test subject having a balance correction abnormality caused by a CNS lesion (cerebellar lesion). These results were obtained by rotating the support surface backward, i.e., pitch toe-up. The exemplary operator display 110 includes five time history graphs including various response measures for the examination trial period of 1 second. In each graph, the thick solid line represents the particular response measure for the subject during an examination trial performed with the subject's eyes closed (or eyes open, or with a stabilized virtual reality scene provided to the test subject, depending on the test protocol desired). The thin solid line represents the selected response measure for a normal population during an examination trial under the same visual condition protocol. The time histories provided in the exemplary user display 110 include time histories of the following response measures over the examination trial period: the angular rotation 111 of the support surface (in degrees of, in this case, pitch); the ankle torque 112 (in Nm, derived from signals provided by the force transducers in the support surface 26); the subject's soleus 113 and tibialis anterior 114 responses (each in millivolts, derived from the signals provided by pairs of EMG electrodes 86 placed on the subject 22); and trunk angular velocity 116 (in degrees per second of, in this case, pitch, derived from the signals provided by the body sway sensors 84 placed on the trunk of the subject 22). Anterior-posterior ankle torque 112, and soleus 113 and tibialis anterior 114 responses for the right side of the body are presented in the operator display 110. Lateral ankle torque, left side muscle responses, trunk roll angular velocity, and platform roll angle for the test period, along with other information, may also be displayed as part of the operator display 110, or as a part of another operator display. The operator display 110 also includes the zero latency line 97, derived from the first inflexion of the support surface angular velocity, and a time line 98 extending from time 0 at the zero latency line 97.

The operator display 110 allows a system operator, e.g., a physician, to compare the response measures obtained from the examination trials of a test subject with the examination trial results obtained from a normal sample population under the same visual protocol conditions. In particular, to make a diagnosis, the operator may consider the following response measure information provided in the operator display 110: differences in ankle torque between the test subject and the normal population between 160 and 260 ms after the support surface moves with respect to zero latency 97; differences in the areas between the test subject's EMG responses and those of the normal population between the intervals 40–100 ms, 80–120 ms, 120–220 ms, 240–340 ms, and 350–700 ms, and increases in the trunk angular velocity from the normal trunk angular velocity response. As discussed previously, large differences between the response measures obtained from the examination trial of a test subject and the examination trial results obtained from the normal sample population may be marked automatically on the operator display 110 to indicate clearly such changes. The response measure information from various sources provided to the operator in a highly readable format in the operator display 110 allows an operator, e.g., a physician, to make a rapid and accurate diagnosis of the presence or absence of a balance-correction abnormality. For the exemplary operator display 110 illustrated in FIG. 8, the pattern of the changes in response measures between the examination trial results obtained from the test subject compared to those of the normal population indicate that the test subject has a balance correction abnormality caused by a CNS lesion.

Figure 9:
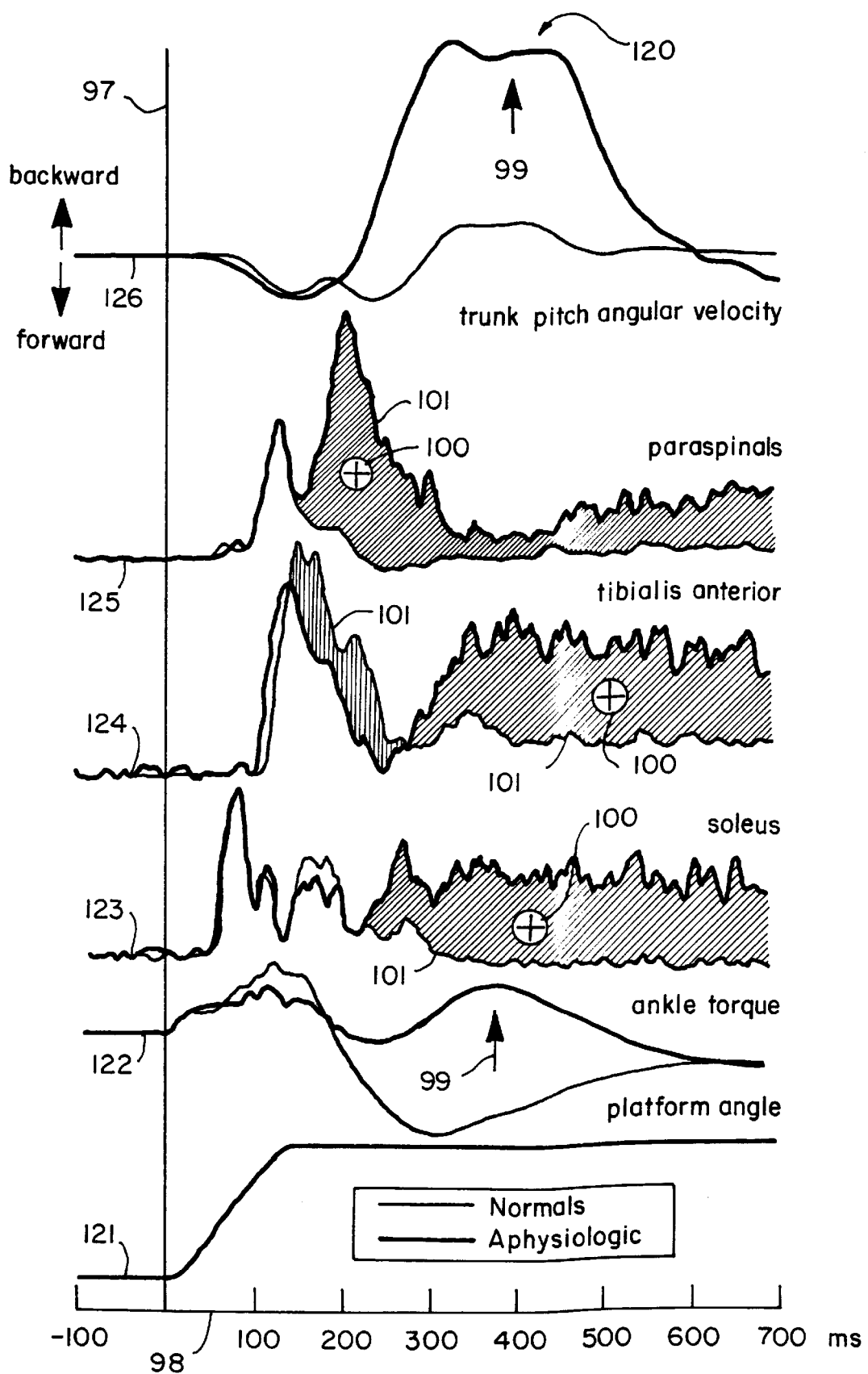
FIG. 9 is an illustration of an exemplary operator's display in accordance with the present invention, providing information derived from various response measures obtained during a pitch toe-up examination trial of a test subject simulating a balance disorder (aphysiologic response pattern).

Another exemplary operator display 120 in accordance with the present invention is illustrated in FIG. 9. This exemplary operator display 120 shows the examination trial results for a test subject having an aphysiologic balance abnormality. These results were obtained by rotating the support surface backward, i.e., pitch toe-up. The exemplary operator display includes six time history graphs including various response measures for the examination trial period of 1 second. In each graph, the thick solid line represents the particular response measure for the subject during an examination trial performed with the subject's eyes closed (or eyes open, or with a stabilized virtual reality scene provided to the test subject, depending on the test protocol desired). The thin solid line represents the selected response measure for a normal population during an examination trial under the same visual condition protocol. The time histories provided in the exemplary user display 120 include time histories of the following response measures over the examination trial period: the angular rotation 121 of the support surface (in degrees of, in this case, pitch); the ankle torque 122 (in Nm, derived from signals provided by the force transducers in the support surface 26); the subject's soleus 123, tibialis anterior 124, and paraspinal 125 responses (each in millivolts, derived from the signals provided by pairs of EMG electrodes 86 placed on the subject 22); and trunk angular velocity 126 (in degrees per second of, in this case, pitch, derived from the signals provided by the body sway sensors 84 placed on the trunk of the subject 22). Anterior-posterior ankle torque 122, and soleus 123, tibialis anterior 124, and paraspinal 125 responses for the right side of the body are presented in the operator display 120. Lateral ankle torque, left side muscle responses, trunk roll angular velocity, and platform roll angle for the test period, along with other information, could also be displayed as part of the operator display 120, or as part of another operator display. The operator display 120 also includes the zero latency line 97, derived from the first inflexion of the support surface angular velocity, and a time line 98 extending from time 0 at the zero latency line 97.

The operator display 120 allows a system operator, e.g., a physician, to compare the response measures obtained from the examination trial of a test subject with the examination trial results obtained from a normal sample population under the same visual protocol conditions. In particular, to make a diagnosis, an operator may consider the following response measure information provided in the operator display 120: differences in ankle torque 122 between the test subject's response and the response of a normal sample population between 160 and 260 ms after the support surface moves with respect to zero latency 97; differences in the areas between the test subject's EMG responses and those of the normal population between the intervals 40–100 ms, 80–120 ms, 120–220 ms, 240–340 ms, and 350–700 ms after zero latency 97; and increases in the trunk angular velocity of the test subject from the normal response. As discussed previously, large differences between the response measures obtained from the examination trial of the test subject and response measures obtained from examination trial of the normal sample population may be marked, e.g., with arrows 99, plus or minus signs 100, and/or highlighting or shading

101, to indicate such differences clearly. The response measure information, from various response measure sources, displayed in the operator display 120 in a highly readable format, allows an operator, e.g., a physician, to make a quick and accurate diagnosis of the presence or absence of a balance-correction abnormality. For the exemplary operator display 120 illustrated in FIG. 9, the pattern of the changes in response measures between examination trial results obtained from the test subject compared to those of the normal population indicate that the test subject has a balance correction abnormality caused by an aphysiologic defect.

Figure 10:
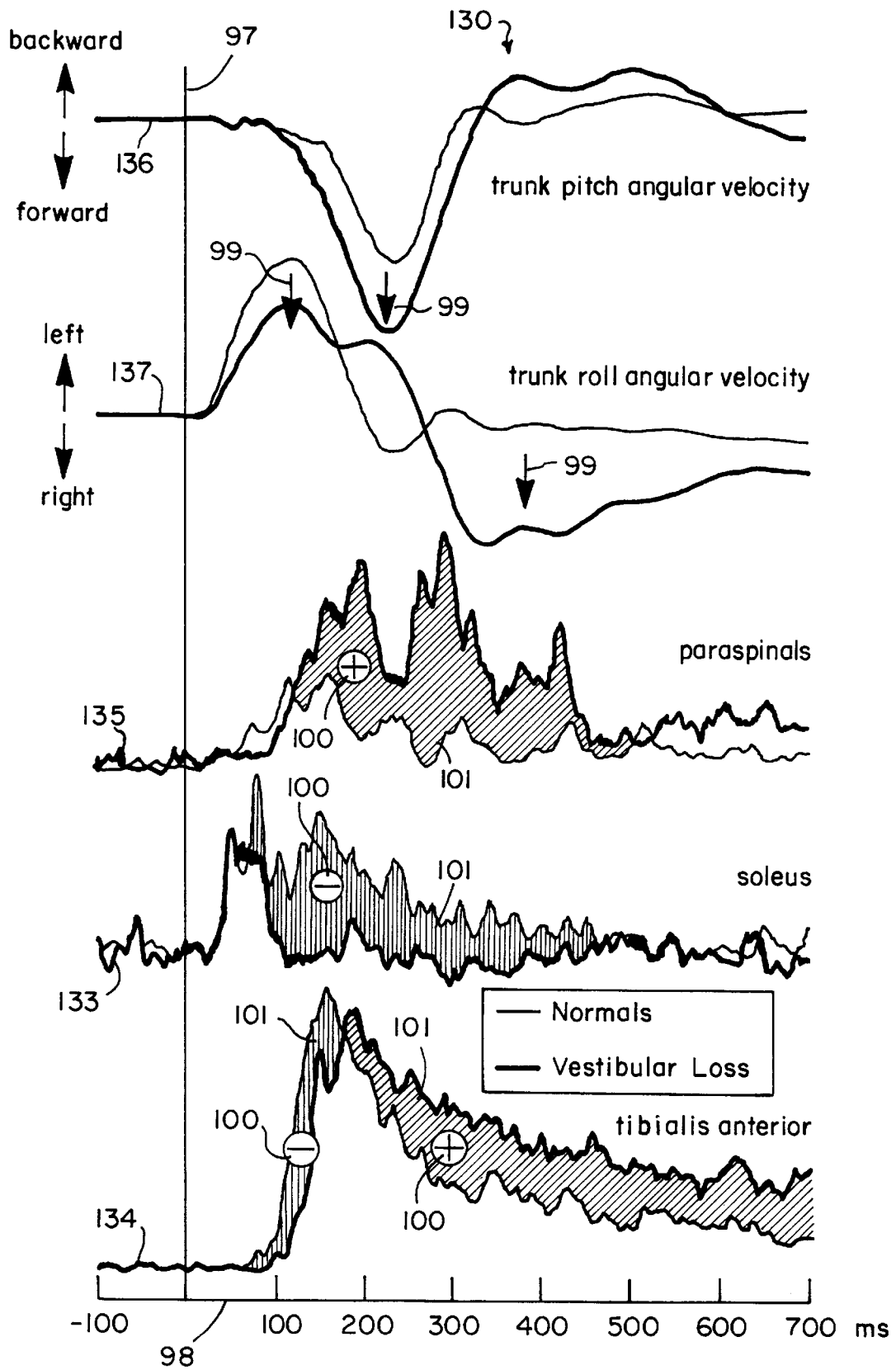
FIG. 10 is an illustration of an exemplary operator's display in accordance with the present invention, providing information derived from various response measures obtained during a pitch back and roll right examination trial of a test subject having a peripheral vestibular deficit.

Another exemplary operator display 130 in accordance with the present invention is illustrated in FIG. 10. This exemplary operator display 130 shows the examination trial results for a test subject having a balance correction abnormality caused by a peripheral vestibular deficit. In this case, the results were obtained by rotating the support surface backward and to the right. The exemplary operator display 130 includes five time history graphs of various response measures for the examination trial period of 1 second. In each graph, the thick solid line represents the particular response measure for the subject during an exam-nation trial performed with the subject's eyes closed (or eyes open, or with a stabilized virtual reality scene provided to the test subject, depending on the test protocol desired). The thin solid line represents the selected response measure for a normal population during an examination trial under the same visual condition protocol. The time histories provided in the exemplary operator display 130 include time histories of the following response measures over the examination trial period: the subject's soleus 133, tibialis anterior 134, and paraspinal 135 responses (each in millivolts, derived from the signals provided by pairs of EMG electrodes 86 placed on the subject 32); and trunk angular velocity in the pitch 136 and roll 137 directions (in degrees per second, derived from the signals provided by the body sway sensors 84 placed on the trunk of the subject). The soleus 133, tibialis anterior 134, and paraspinal 135 responses for the right side of the body are presented in the operator display 130. Ankle torque, left side muscle responses, and support platform pitch and roll angles for the test period, along with other information, could also be displayed as part of the operator display 130, or as a part of another operator display. The operator display 130 also includes the zero latency line 97, derived from the first inflection of the support surface angular velocity, and a time line 98 extending from time 0 at the zero latency line 97.

The operator display 130 allows a system operator, e.g., a physician, to compare the response measures obtained from the examination trial of a test subject with the examination trial results obtained from a normal sample population under the same visual protocol conditions. For example, to perform a diagnosis, an operator may consider the following response measure information presented on the operator display 130: differences in the areas between the test subject's EMG responses and those of the normal population between the intervals 40–100 ms, 80–120 ms, 120–220 ms, 240–340 ms, and 350–700 ms, following zero latency 97; and increases in the trunk pitch and roll angular velocities of the test subject from the angular velocity responses of the normal population. As discussed previously, large differences in the response measures obtained from the examination trial of a test subject and the examination trial results obtained from a normal sample population may be marked on the operator display 130, e.g., using arrows 99, plus or minus signs 100, and/or highlighted or shaded areas 101, to indicate clearly such large differences. The response measure information from various sources provided to the operator in an easily readable form on the operator display 130, allows an operator, e.g., a physician, to make a diagnosis of the presence or absence of a balance-correction abnormality. For the exemplary operator display 130 illustrated in FIG. 10, the pattern of changes in response measures between the examination trial results obtained from the test subject compared to those of the normal population indicate that the test subject has a balance correction abnormality caused by a peripheral vestibular deficit.

Figure 11:
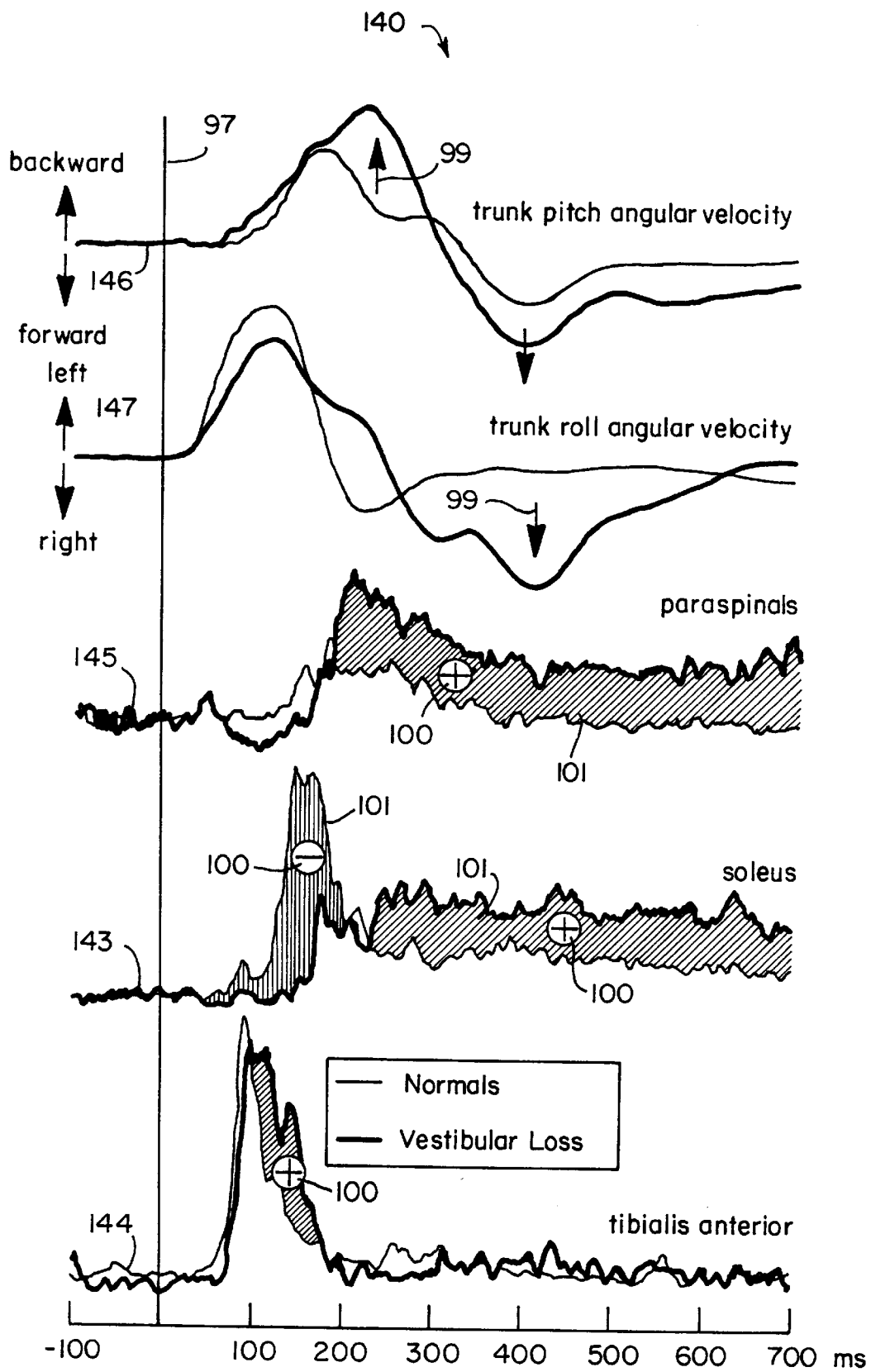
FIG. 11 is an illustration of an exemplary operator's display in accordance with the present invention, providing information derived from various response measures obtained during a pitch forward and roll right examination trial of a test subject having a peripheral vestibular deficit.

Yet another exemplary operator display 140 in accordance with the present invention is illustrated in FIG. 11. This exemplary operator display shows the examination trial results for a test subject having a balance correction abnormality caused by a peripheral vestibular deficit. In this case, however, the results were obtained by rotating the support surface forward and to the right. The exemplary operator display 140 includes five time history graphs of various response measures for the examination trial period of 1 second. In each graph, the thick solid line represents the particular response measure for the subject during an examination trial performed with the subject's eyes closed (or eyes open, or with a stabilized virtual reality scene provided to the test subject, depending on the test protocol desired). The thin solid line represents the selected response measure for a normal population during an examination trial under the same visual condition protocol. The time histories provided in the exemplary user display 140 include time histories of the following response measures over the examination trial period: the subject's soleus 143, tibialis anterior 144, and paraspinal 145 responses (each in millivolts, derived from the signals provided by pairs of EMG electrodes 86 placed on the subject 22); and trunk pitch 146 and roll 147 angular velocity (in degrees per second, derived from the signals provided by the body sway sensors 84 placed on the trunk of the subject 22). Soleus 143, tibialis anterior 144, and paraspinal 145 responses for the right side of the body are presented in the operator display 140. Ankle torque, left side muscle responses, and support platform angles for the test period, along with other information, could also be displayed as part of the operator display 140, or as part of another operator display. The operator display 140 also includes the zero latency line 97, derived from the first inflexion of the support surface angular velocity, and a time line 98 extending from time 0 at the zero latency line 97.

The operator display 140 allows a system operator, e.g., a physician, to compare the response measures obtained from the examination trials of a test subject with the examination trial results obtained from a normal sample population under the same visual protocol conditions. For example, to make a diagnosis, an operator may consider the following response measure information provided on the operator display 140: differences in the areas between the test subject's EMG responses and those of the normal population between the intervals 40–100 ms, 80–120 ms, 120–220 ms, 240–340 ms, and 350–700 ms after zero latency 97; and increases in the trunk angular velocity of the test subject from those of a normal population. As discussed previously, large differences between response measures obtained from the examination trial of the test subject and the examination trial results obtained from the normal sample population may be marked on the operator display 140, e.g., using arrows 99, plus or minus signs 100, and/or differently shaded or highlighted areas 101, to indicate clearly such large differences. The response measure information from various sources, provided on the operator display 140 in a highly readable format, allows an operator, such as a physician, to make a diagnosis of the presence or absence of a balance correction abnormality. In the exemplary operator display 140 illustrated in FIG. 11, the pattern of changes in response measures between the examination trial results obtained from the test subject compared to those of the normal population indicate that the test subject has a balance correction abnormality caused by a peripheral vestibular deficit.

Note that the operator displays 90, 130, and 140 in FIGS. 6, 10, and 11, respectively, each show response measures obtained from a test subject having a balance correction abnormality caused by a peripheral vestibular deficit. However, each set of response measures was obtained by rotating the support surface in a different direction, i.e., backward for operator display 90 in FIG. 6, backward and to the right for operator display 130 in FIG. 10, and forward and to the right for operator display 140 in FIG. 11. By considering the response measure information provided in each of these displays, an operator, such as a physician, can determine not only that a balance correction abnormality exists and the cause of the balance correction abnormality, e.g., a peripheral vestibular deficit, but also the direction in which the abnormality has its greatest effect. For example, by comparing the operator displays 90, 130, and 140 illustrated in FIGS. 6, 10, and 11, respectively, an operator can see that the exemplary test subject having a peripheral vestibular deficit is most unstable for support surface rotations backward and to the right.

For each of the exemplary operator displays 90, 102, 110, 120, 130, and 140, illustrated in FIGS. 6–11, it should be noted that time histories for more, fewer, or different response measures than those illustrated in the exemplary operator displays may be included in similar operator displays in accordance with the present invention. Furthermore, such operator displays may also simultaneously display response measures for different examination trials of the same test subject, perhaps using different visual protocol conditions or before and after the test subject has been provided therapy. Such displays may include time histories similar to those illustrated by example herein, but wherein the results of different examination trials, rather than those for the test subject and a normal population, are displayed simultaneously.

Figure 12:
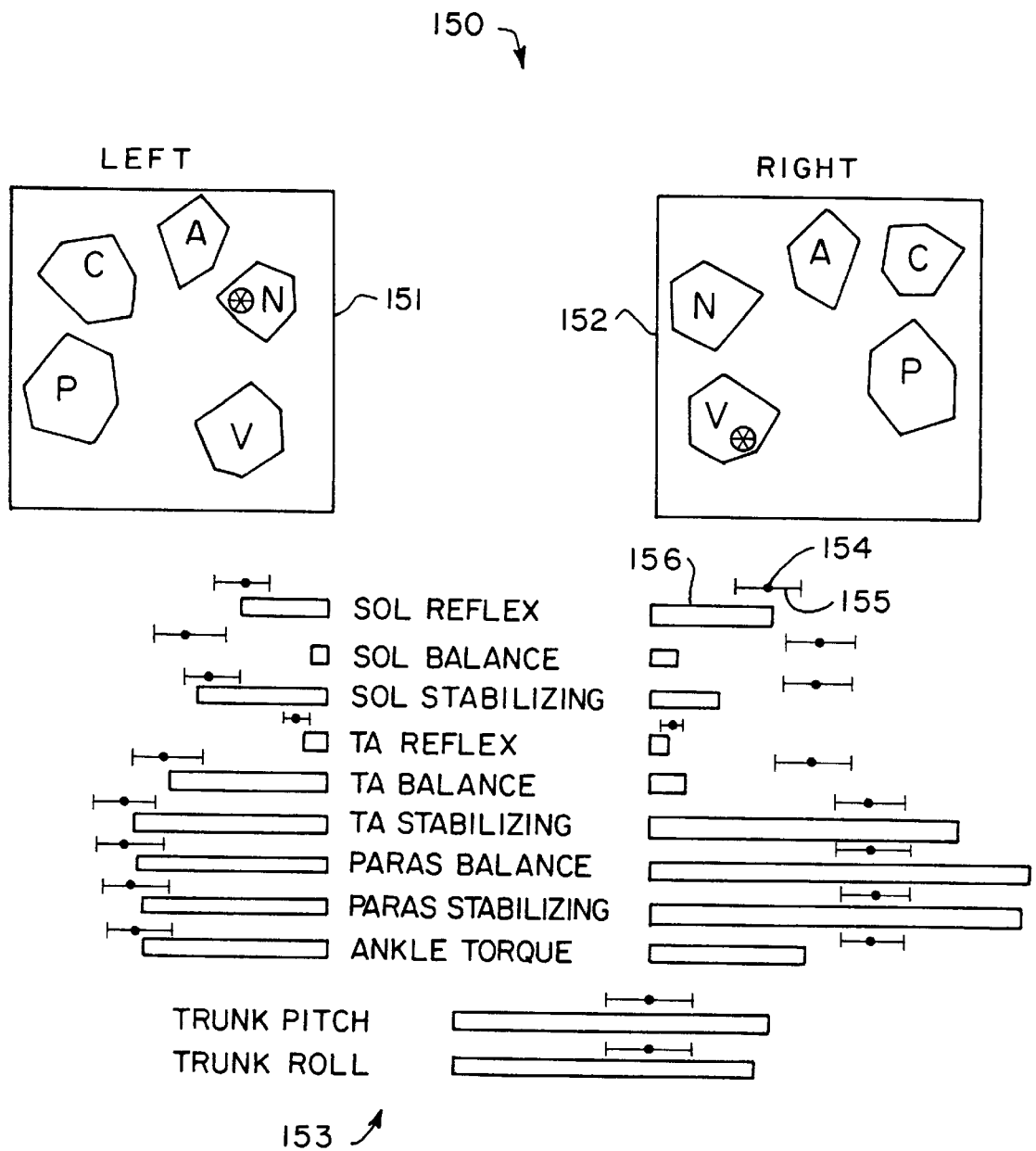
FIG. 12 is an illustration of an exemplary summary operator's display in accordance with the present invention, indicating the classification of a test subject's left and right side balance corrections for a pitch backward and roll right support surface movement, and providing a comparison of various test subject response measures to the response measure bounds of normal subjects.

An operator, such as a physician, may diagnose whether a subject has a balance correction abnormality, the direction of the subject's greatest instability, and whether the cause of the balance correction abnormality is vestibular, proprioceptive, CNS lesion, or aphysiologic in origin, from the time histories of response measures which are provided in the exemplary operator displays 90, 102, 110, 120, 130, and 140, previously described. A balance disorder diagnosis and rehabilitation system in accordance with the present invention preferably also provides an automatic diagnosis of balance correction abnormalities, including the side of the abnormality and the probable cause. The results of such an automatic diagnosis may preferably be displayed to an operator on the operator display unit 30. An exemplary operator display 150 providing such an automatic diagnosis is illustrated in FIG. 12.

In order to perform the automatic diagnosis, a step-wise discriminant analysis on response measures obtained from a normal sample population, and subjects known to have vestibular, proprioceptive, CNS lesion, or aphysiologic deficits, is performed. Step-wise discriminant analysis is a conventional statistical analysis technique which is used to assign weights to each response measure in order to achieve a maximum separation between normal and different abnormal population responses. The step-wise discriminant analysis is preferably performed for response measures obtained from the left and right sides of the required sample populations. In this way, normal, vestibular, proprioceptive, CNS lesion, and aphysiologic population groups are obtained for the left and right sides of a subject. These population groups are displayed at the top of the exemplary operator display 150 of FIG. 12, for the left 151 and right 152 sides, and are labelled N, V, P, C, and A, respectively.

The operator display 150 illustrated in FIG. 120 shows the results of an examination trial performed on a subject 22, wherein the support surface is tilted back and to the right to perturb the subject's stance. The lower half 153 of the exemplary operator display 150 illustrates, in bar chart form, selected response measures for the subject during selected portions of the examination trial. Examples of such response measures which may be displayed in bar chart form include: trunk angular velocity maxima during the trial period; EMG responses between, e.g., 40–100 ms or 80–120 ms after support surface flexion (reflex), 120–220 ms after support surface flexion (balance), or 350–700 ms after support surface flexion (stabilizing); and changes in ankle torque between 160 and 260 ms after support surface flexion. In this case, the displayed response measures include: left and right soleus response, left and right tibialis anterior response, left and right paraspinalis response, left and right ankle torque, trunk roll (which, in this case, is to the left), and trunk pitch (which, in this case, is in the forward direction). Means 154 and standard deviations 155 of responses for these response measures for a normal sample population are illustrated along with the bars 156 representing the test subject's response during the examination trial. As can be seen from the exemplary operator display 150 in FIG. 12, most of the left side response measures of the test subject fall within the range of responses obtained from a normal sample population. However, for the test subject's right side, the tibialis anterior balance response is less than normal, the tibialis anterior stabilizing response is greater than normal, the paraspinalis responses are greater than normal, ankle torque is less than normal, and the trunk pitch and roll angular velocity is greater than normal.

The weightings obtained by step-wise discriminant analysis on known populations are applied to the response measures obtained from the test subject. The results are plotted at the top of the operator display 150 for the left 151 and right 152 side of the test subject. In this exemplary case, the results of the examination trial indicate that the subject's balance correction on the left side falls within the normal sample population group, however, the subject's balance correction on the right side falls within a population grouping of those having a vestibular deficit. It should be understood that more, fewer, or different response measures than those displayed in the exemplary operator display 150 may be used to perform automatic balance correction abnormality diagnosis in accordance with the present invention.

Figure 13:
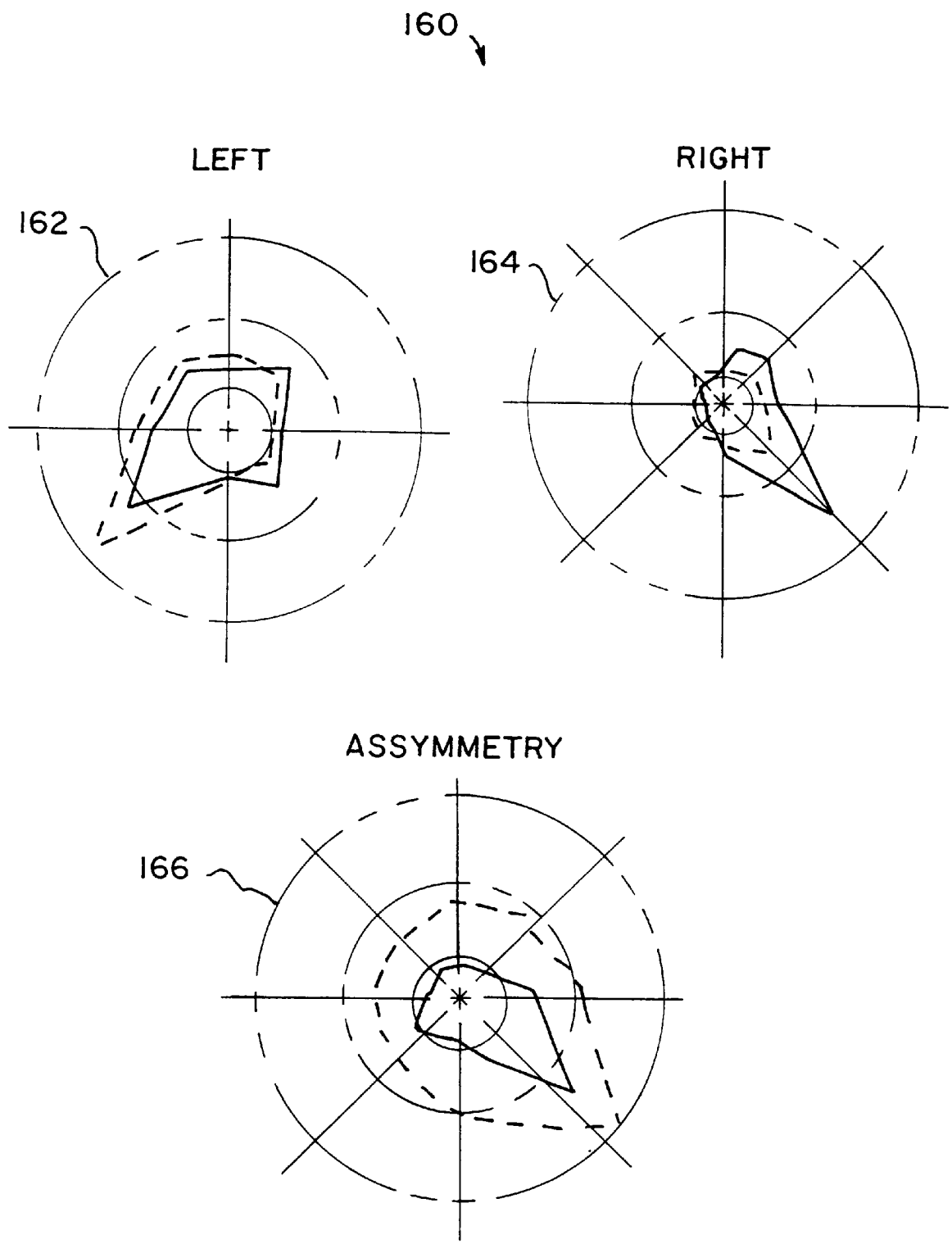
FIG. 13 is an illustration of an exemplary operator's display in accordance with the present invention, providing left and right response measure information for all directions of support surface movement and providing an indication of the degree of the asymmetry of a test subject's response measures for different directions of support surface movement.

A balance disorder diagnosis and rehabilitation system in accordance with the present invention is also preferably capable of providing to an operator a display of those response measures of most interest for all directions of support platform tilt. This information may be displayed to the operator in the form of polar plots, as illustrated in the exemplary operator display 160, shown in FIG. 13. Polar plots for a selected response measure of interest are preferably provided for the left 162 and right 164 sides of the test subject. The polar plots may show the examination trial results for several different examination protocols. For example, in the exemplary operator display 160, the value of the selected response measure is shown for an examination trial with the test subject's eyes open (solid line) and for an examination trial with the test subject's eyes closed (dashed line). A third polar plot 166 may be provided to show a measure of the asymmetry between different response measures for a test subject. Since each of the polar plots 162, 164, and 166 shows response measure or response measure asymmetry values for all directions of support surface movement, it is apparent that a test protocol must be run in which the support surface is tilted in a variety of different directions in order to obtain the necessary data to generate the polar plots 162, 164, and 166. Polar plots, such as those illustrated in the exemplary operator display 160 of FIG. 13, may be used by an operator to establish the direction of major pathology of the subject and/or to determine if a rehabilitory protocol, whether it be in the form of feedback to be described in more detail below, or otherwise, has had an effect in improving the subject's balance correction capabilities. Furthermore, if the direction of a subject's greatest instability can be established by testing balance in different directions, the procedure for classifying the cause of instability can be applied for that direction and also for the right and left sides of the body. Testing in any direction other than forward-backward will naturally lead to asymmetries in responses in normal subjects. The failure of the appearance of normal left-right asymmetries will provide valuable information on the balance disorder.

A balance disorder diagnosis and rehabilitation system in accordance with the present invention preferably also provides feedback to the test subject of his balance correction responses. The information provided to the subject is used by the subject to augment the balance signals normally used by the subject's brain to correct his body sway instabilities during motion of the support surface. Feedback may be in the form of visual, auditory, or tactile information, or in the form of direct electrical stimulation of the vestibular nerve, or a combination of such feedback types.

Figure 2:
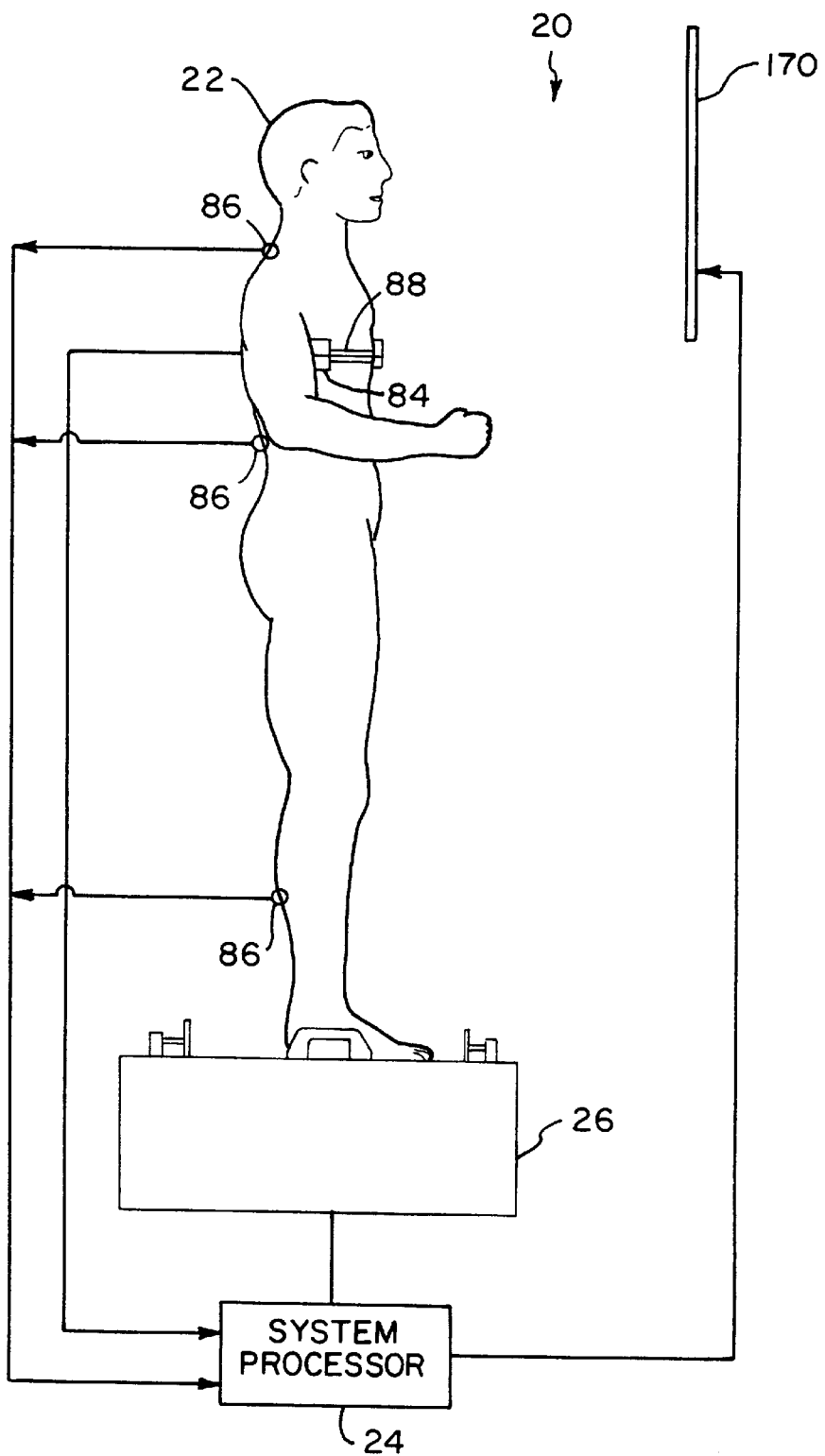
FIG. 2 is a schematic illustration of a human subject placed in a standing position on an exemplary embodiment of a balance disorder diagnosis and rehabilitation system in accordance with the present invention.

A system 40 for providing visual feedback may include a subject feedback display 170, such as a monitor screen, mounted at eye level in front of the subject 22, as illustrated in FIG. 2. The subject feedback display screen 170 may be mounted on a stand, wall, or using any other convenient mounting technique. The subject feedback display 170 is preferably mounted approximately one meter distant from the subject 22.

Figure 14:
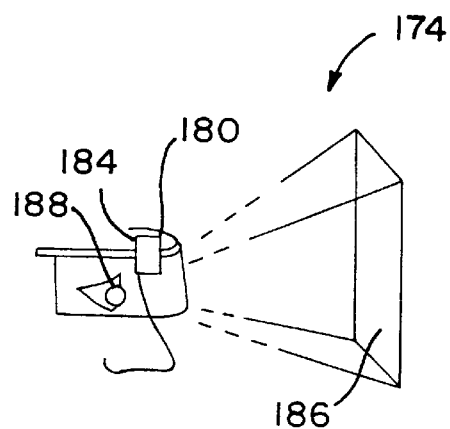
FIG. 14 is an illustration of an exemplary visual balance correction feedback system in accordance with the present invention.

An alternative, and preferred system 174 for providing visual subject feedback is described with reference to FIG. 14. This preferred visual feedback system 174 includes a pair of eyewear 180 which are worn by the subject 22. An image is projected into the subject's eye 188 by a monocular virtual imaging system 184 which may be mounted on the pair of eyewear 180. The imaging system 184 is preferably capable of projecting, at least, a standard VGA 640 by 480 pixel image that may be either monochrome or in color. A preferred imaging system 184 that may be used is the model Mark I or Mark II monochrome imaging system or model Mark III color imaging system, manufactured by Seattle Site Sys., Inc. of Redmond, Wash., U.S.A. It should be noted that other image projection systems for projecting images into a subject's eyes, including a computer display image projection system which provides a binocular, stereoscopic image, might also be used to provide visual feedback in accordance with the present invention. By appropriate focusing of the image, by altering the distance between the LCD display and the lens in the imaging system 184, the image may be made to appear to the subject 22 as a large image 186, e.g., 1.5 meters across, floating in front of the subject at a distance, e.g., of three meters. The eyewear 180 may or may not be light blocking. Thus, the subject 22 may be able to view both the world around him and the image 186 simultaneously through the eyewear 183 if the eyewear 180 are not light blocking and the visual feedback image is stabilizing, to improve balance control, or may be able only to view the visual feedback image 186, if the eyewear 180 are light blocking and the visual feedback image is destabilizing, to test the efficacy of visual inputs to balance control. Although the image 186 is illustrated in FIG. 14 as being projected into the right eye 188 of the subject 22, the projection system 184 might also be used to project the image into the left eye of the subject 22. Preferably, the image projection system 184 is mounted on the eyewear 180 so as to project the image such that the image is viewed by the subject's dominant eye.

The image projected into the subject's eye 188 may provide visual feedback to the subject of one or more of the response measures obtained from the signals provided by the force transducers 82, the body sway sensors 84, or the EMG electrodes 86. For example, the image projected into the subject's eye 188 may provide visual feedback to the subject of his body sway angle and angular velocity as obtained from the body sway sensors 84. The subject 22 may use this information to augment the balance signals normally used by his brain to correct his body sway instabilities. In this case, the eyewear 180 should not be light blocking, i.e., should allow viewing of the surrounding world, and the visual feedback presented to the subject should enhance balance control.

Figure 15:
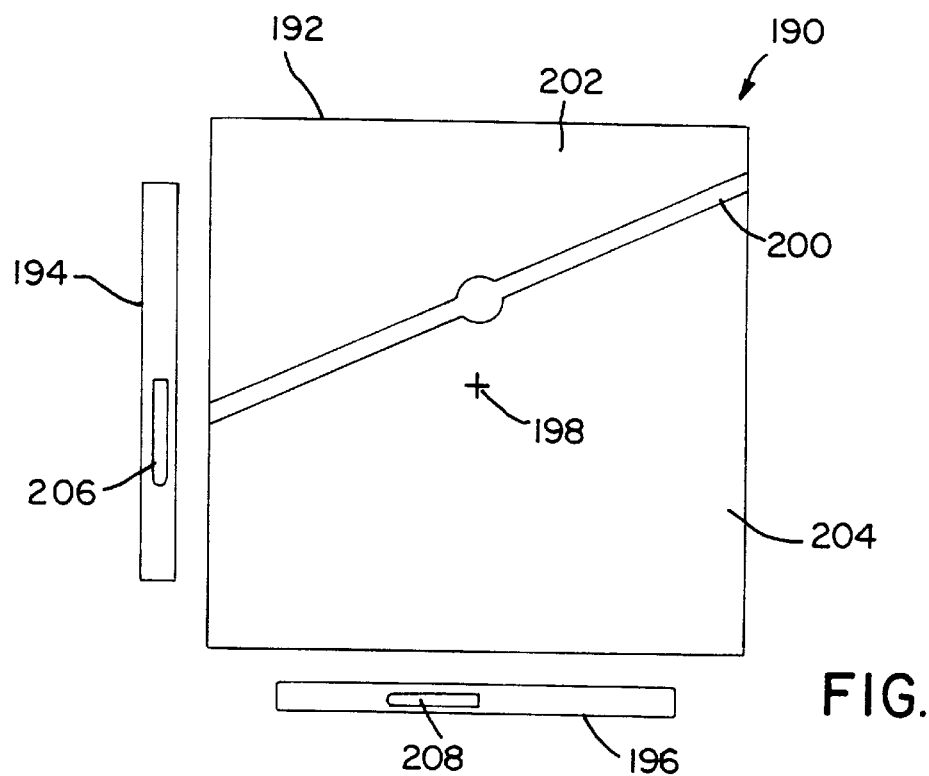
FIG. 15 is an illustration of an exemplary balance correction feedback display in accordance with the present invention.

A preferred format for providing visual feedback of the subject's body sway angle and angular velocity is illustrated in FIG. 15. A visual feedback display 190 includes a central frame display 192 and boundary frame displays 194 and 196. The information contained in the central frame 192 and boundary frame 194 and 196 displays relates to the sway deviations from a point of reference 198. The preferred point of reference 198 is a standing point of reference which is re-set by either the subject or the system operator when the subject 22 is standing quietly with a sway velocity of less than one degree per second in both roll and pitch directions.

The central frame display 192 includes a substantially horizontally oriented bar 200 that divides the central frame display 192 into top and bottom fields 202 and 204. The top field 202 is preferably colored or shaded more lightly than the bottom field 204, with the bar 200 colored or shaded at an intermediate intensity level. The horizontal bar 200 moves upward in the central frame 192 when the subject's upper body sways forward, and moves downward, toward the bottom of the central frame 192, when the subject's upper body sways backward. Thus, the area of the dark colored field 204 increases and the area of the light colored field 202 decreases with forward sway, and the area of the dark colored field 204 decreases, and the area of the light colored field 202 increases with backward sway. The angle of the bar 200 within the central frame 192 represents roll to the left or right of the subject's upper body. A forward pitch and a leftward roll of the subject's torso is thus illustrated in FIG. 15. Bar graphs 206 and 208 in the boundary frames 194 and 196 indicate the exact amounts of pitch and roll, respectively. The width of the bar 200 in the central frame 192 increases or decreases in relation to the vectorial combination of roll and pitch velocities of the subject's upper body.

The sensitivity of the movements of the central bar 200 with respect to angular sway deviations, and the sensitivity of the width of the central bar 200 with respect to the angular velocity of the subject's upper body, are preferably variable parameters. These variable parameters represent the visual feedback gain of the system. The visual feedback gain parameters may be set by the operator to help improve the subject's balance control. The visual feedback gain parameters may be fine tuned by repeated examination trials employing the diagnostic information provided in the operator displays 90, 102, 110, 120, 130, 140, 150, and 160.

Response measure information derived from the force transducer 82, body sway sensor 84, and EMG electrode 86 signals may also be provided to the subject aurally, using conventional audio headphones, an aural probe for insertion into the external ear canal of the subject's ear, or the like. For example, body sway information obtained from the body sway sensors 84 may be provided to the subject 22 in the form of auditory feedback. In a preferred embodiment of an auditory feedback system 42, pitch angular displacements of the subject's upper body are presented as a tone formed by frequency modulations around a first center frequency of, e.g., 1500 Hz, and roll angular displacements are presented as a tone formed by frequency modulations around a second center frequency of, e.g., 500 Hz. Increased velocity of angular sway may be presented as an increase in the volume of the audible tones, ranging from the subject's hearing threshold at the first and second center frequencies to, for example, 20 dB less than the subject's maximum comfortable level at these frequencies. For the auditory feedback system 42, the depth of frequency modulation and the volume of the audio signals with respect to the body sway angle and angular velocity are preferably variable parameters of the auditory feedback gain. The feedback gain parameters may be set by the operator to help improve the subject's balance control during movement of the support surfaces 26.

For tactile feedback 44, vibrators may be used to provide response measure feedback to the subject 22. For example, two vibrators, each placed in a different position on the body, and operating at, e.g., 250 Hz, may be used to provide body sway angle and angular velocity feedback, obtained from the body sway sensors 84, for one of the pitch or roll directions. A sense of forward and backward body sway may be conveyed by modulation of the frequency of vibration of the vibrators in relation to the angular velocity of sway. The amplitude of the vibration corresponds to the angle of sway deviation. A similar pair of vibrators may be used to convey a sense of sway in the roll direction. For the tactile feedback system 44, the depth of frequency modulation of the vibrators and the amplitude of the vibration with respect to the body sway angle and angular velocity are preferably variable parameters of the tactile feedback gain. These feedback gain parameters may be set by the operator to help improve the subject's control of sway, and, therefore, improve the subject's balance control.

Feedback of the response measures obtained from the force transducers 82, body sway sensors 84, and/or EMG electrodes 86 during an examination trial may also be provided in the form of varying electrical signals that are used to directly stimulate the vestibular nerve. Such signals are sensed by the subject 22 as a change in the angle and/or linear position of the subject's head. Feedback signals for direct electrical stimulation of the vestibular nerve may be transmitted transcutaneously to an implantable device directly connected via electrodes to the close proximity of the vestibular nerve, or to the nerve itself. The pulse rate, amplitude, and duty cycle of the electrical stimulation provided at the electrodes may, for example, be varied according to the body sway angle and body sway angular velocities as determined by the system processor 24 based on the response measure signals obtained from the body sway sensors 84. As with the visual 40, auditory 42, and tactile 44 feedback systems, the feedback gains of the system 46 for providing direct electrical stimulation of the vestibular nerve are preferably variable parameters that may be set by the operator to help improve the subject's balance control.

Feedback of response measures to the subject 22 may preferably be provided during an examination trial, when the support surfaces is in motion, to help the subject stabilize himself more rapidly when his stance is perturbed by the motion of the support surface. Such feedback may also be used to ensure that the subject is as close as possible to his normal "upright" position prior to the imposition of the support surface movement during the examination trial. Once the movement of the support surface starts, the feedback may be turned off.

Feedback may also be used for diagnosis, rather than rehabilitory purposes. For example, a visual scene may be displayed to the subject 22 and moved in such a manner that the subject 22 is more easily destabilized by the support surface movement. This can be accomplished, for example, using the visual feedback system 174 described with reference to FIG. 14, wherein the light-weight eyewear 180 are light-blocking. In this case, the subject will only see the projected image. The visual scene displayed to the subject 22, to destabilize the subject, can be used for diagnostic purposes such as establishing the balance correction sensitivity of the subject to visual inputs, either in combination with or separate from the support platform 26 of the present invention.

It should be understood that this invention is not confined or limited to the particular embodiments, implementations, and applications herein illustrated and described, but embraces all such modified forms thereof as come within the scope of the following claims.

What is claimed is:

1. An apparatus for diagnosing balance correction abnormalities in a subject, comprising:
   (a) a rotatable support surface for supporting the subject and capable of rotation in pitch and roll directions;
   (b) support surface control means responsive to support surface control signals for rotating the support surface in the pitch and roll directions;
   (c) means for measuring a response of the subject to the rotation of the support surface and for providing response measure signals corresponding to the subject's response; and
   (d) system processor means for generating the support surface control signals, receiving the response measure signals, and generating an operator display from the response measure signals.

2. The apparatus for diagnosing balance correction abnormalities of claim 1 wherein the means for measuring a response of the subject to the rotation of the support surface includes means for measuring separate left and right side responses of the subject.

3. The apparatus for diagnosing balance correction abnormalities of claim 1 wherein the means for measuring a response of the subject to the rotation of the support surface includes at least one of:
   (a) a body sway sensor attached to the subject's body for measuring sway of the subject's body in response to rotation of the support surface;
   (b) center-of-foot pressure measurement means for measuring changes in the subject's center-of-foot pressure or ankle torque in response to rotation of the support surface; and
   (c) EMG measurement means for measuring the electromyographic responses of a subject's muscle to rotation of the support surface.

4. An apparatus for diagnosing balance correction abnormalities in a subject, comprising:
   (a) a rotatable support surface for supporting the subject and capable of rotation in pitch and roll directions;
   (b) support surface control means responsive to support surface control signals for rotating the support surface in the pitch and roll directions;
   (c) a body sway sensor including velocity transducers attached to the subject's body to measure the pitch and roll angular velocity of the subject's body in response to the rotation of the support surface and for providing response measure signals corresponding to the subject's response; and
   (d) system processor means for generating the support surface control signals, receiving the response measure signals, and generating an operator display from the response measure signals.

5. The apparatus for diagnosing balance correction abnormalities of claim 3 wherein the center-of-foot pressure measurement means includes force transducers mounted on or within the support surface to measure the anterior-posterior and lateral change in center-of-foot pressure or ankle torque of the subject.

6. The apparatus for diagnosing balance correction abnormalities of claim 3 wherein the EMG measurement means includes electromyographic electrodes placed over muscles on the left and right sides of the subject's body.

7. The apparatus for diagnosing balance correction abnormalities of claim 1 wherein the operator display includes a time history display of the response measure.

8. The apparatus for diagnosing balance correction abnormalities of claim 7 comprising additionally means for storing response measures and wherein the time history display includes a time history display of a stored response measure.

9. The apparatus for diagnosing balance correction abnormalities of claim 8 wherein the stored response measures are response measures obtained from a normal sample population.

10. The apparatus for diagnosing balance correction abnormalities of claim 1 wherein the operator display includes a display of the response measure for a plurality of directions of support surface rotation.

11. The apparatus for diagnosing balance correction abnormalities of claim 10 wherein the operator display includes a polar plot of the response measure for a plurality of directions of support surface rotation.

12. The apparatus for diagnosing balance correction abnormalities of claim 10 wherein the operator display includes a display of the response measure for a right side of the subject for a plurality of directions of support surface rotation and a display of the response measure for a left side of the subject for a plurality of directions of support surface rotation.

13. The apparatus for diagnosing balance correction abnormalities of claim 1 wherein the operator display includes a bar chart display of the response measure for a selected time period during or after support surface rotation.

14. The apparatus for diagnosing balance correction abnormalities of claim 13 wherein the operator display includes a bar chart display of the response measure for right and left sides of the subject for a selected time period during or after support surface rotation.

15. The apparatus for diagnosing balance correction abnormalities of claim 1 wherein the system processor means includes diagnosis means for diagnosing the presence or absence of a balance correction abnormality from the response measure.

16. The apparatus for diagnosing balance correction abnormalities of claim 15 wherein the diagnosis means includes classification means for classifying the response measure as belonging either to a normal group or to one of one or more of the groups of subjects having pathological responses selected from the group of groups of subjects having pathological responses consisting of: a vestibular deficit group, a proprioceptive deficit group, a central nervous system lesion group, and an aphysiological group.

17. An apparatus for diagnosing balance correction abnormalities in a subject, comprising:
(a) a rotatable support surface for supporting the subject and capable of rotation in pitch and roll directions;
(b) support surface control means responsive to support surface control signals for rotating the support surface in the pitch and roll directions;
(c) means for measuring a response of the subject to the rotation of the support surface and for providing response measure signals corresponding to the subject's response; and
(d) system processor means for generating the support surface control signals, receiving the response measure signals, generating an operator display from the response measure signals, and diagnosing the presence or absence of a balance correction abnormality from the response measure including means for classifying the response measure as belonging either to a normal group or to one of one or more groups of subjects having pathological responses including means for weighting the response measure using a weighting obtained from a step-wise discriminant analysis on known normal and pathological population groups.

18. The apparatus for diagnosing balance correction abnormalities of claim 1 comprising additionally feedback means for providing feedback of the response measure to the subject.

19. The apparatus for diagnosing balance correction abnormalities of claim 18 wherein the feedback means includes means for providing feedback of the response measure to the subject in at least one form selected from the group of forms of feedback consisting of: visual feedback, auditory feedback, tactile feedback, and feedback by electrical stimulation of the vestibular nerve.

20. The apparatus for diagnosing balance correction abnormalities of claim 18 wherein the feedback means includes a virtual imaging system mounted on a pair of eyewear.

21. The apparatus for diagnosing balance correction abnormalities of claim 20 wherein the pair of eyewear are substantially light transmitting and wherein the system processor includes means for controlling the virtual imaging system to provide a virtual feedback image to the subject corresponding to the response measure whereby the subject's balance correction is stabilized.

22. The apparatus for diagnosing balance correction abnormalities of claim 20 wherein the pair of eyewear are substantially light blocking and wherein the system processor includes means for controlling the virtual imaging system to provide a virtual feedback image to the subject corresponding to the response measure whereby the subject's balance correction is destabilized.

23. An apparatus for diagnosing balance correction abnormalities in a subject, comprising:
(a) a rotatable support surface for supporting the subject and capable of rotation in pitch and roll directions;
(b) support surface control means responsive to support surface control signals for rotating the support surface in the pitch and roll directions and for providing support surface angle signals corresponding to the angle of rotation of the support surface in the pitch and roll directions;
(c) body sway sensors attached to the subject's body for measuring sway of the subject's body in response to rotation of the support surface and providing subject body sway signals corresponding to the subject's measured body sway;
(d) center-of-foot pressure measurement means for measuring changes in the subject's center-of-foot pressure or ankle torque in response to rotation of the support surface and providing subject center-of-foot pressure signals corresponding to the subject's changes in center-of-foot pressure or ankle torque;
(e) EMG measurement means for measuring the electromyographic responses of a subject's muscles to rotation of the support surface and providing subject EMG signals corresponding to the subject's muscle responses; and
(f) system processor means for generating the support surface control signals, receiving the support surface angle signals and the subject body sway, center-of-foot pressure, and EMG signals, and generating an operator display from the support surface angle signals and the subject body sway, center-of-foot pressure, and EMG signals.

24. The apparatus for diagnosing balance correction abnormalities of claim 23 wherein the operator display includes simultaneously displayed time histories of the rotation of the support surface, and the subject's body sway, changes in center-of-foot pressure or ankle torque, and muscle responses.

25. The apparatus for diagnosing balance correction abnormalities of claim 24 comprising additionally means for storing body sway, changes in center-of-foot pressure or ankle torque, and muscle response information, and wherein the displayed time histories include simultaneously displayed stored body sway, changes in center-of-foot pressure or ankle torque, and muscle responses.

26. The apparatus for diagnosing balance correction abnormalities of claim 25 wherein the stored body sway, changes in center-of-foot pressure or ankle torque, and muscle response information is obtained from a normal sample population.

27. The apparatus for diagnosing balance correction abnormalities of claim 23 wherein the system processor means includes diagnosis means for automatically diagnosing the presence or absence of a balance correction abnormality from the subject body sway, center-of-foot pressure, and EMG signals.

28. The apparatus for diagnosing balance correction abnormalities of claim 27 wherein the diagnosis means includes classification means for weighting and combining body sway, center-of-foot pressure, and muscle response information derived from the subject body sway, center-of-foot pressure, and EMG signals and for classifying the weighted and combined body sway, center-of-foot pressure, and muscle response information as belonging either to a normal group or to one of one or more of the groups of subjects having pathological responses selected from the group of groups of subjects having pathological responses consisting of: a vestibular deficit group, a proprioceptive deficit group, a central nervous system lesion group, and an aphysiological group.

29. The apparatus for diagnosing balance correction abnormalities of claim 28 wherein the weightings are obtained from a step-wise discriminant analysis on known normal and pathological population groups.

30. An apparatus for diagnosing balance correction abnormalities in a subject, comprising:
  (a) a rotatable support surface for supporting the subject and capable of rotation in pitch and roll directions;
  (b) support surface control means responsive to support surface control signals for rotating the support surface in the pitch and roll directions;
  (c) means for measuring left and right side responses of the subject to the rotation of the support surface and for providing left and right side response measure signals corresponding to the subject's response; and
  (d) system processor means for generating the support surface control signals, receiving the left and right side response measure signals, and automatically diagnosing the presence or absence and side of a balance correction abnormality from the left and right side response measure signals.

31. The apparatus for diagnosing balance correction abnormalities of claim 30 wherein the system processor means includes classification means for classifying the response measure for each of the left and right sides of the subject as belonging either to a normal group or to one of one or more of the groups of subjects having pathological responses selected from the group of groups of subjects having pathological responses consisting of: a vestibular deficit group, a proprioceptive deficit group, a central nervous system lesion group, and an aphysiological group.

32. An apparatus for diagnosing balance correction abnormalities in a subject, comprising:
  (a) a rotatable support surface for supporting the subject and capable of rotation in pitch and roll directions;
  (b) support surface control means responsive to support surface control signals for rotating the support surface in the pitch and roll directions;
  (c) means for measuring left and right side responses of the subject to the rotation of the support surface and for providing left and right side response measure signals corresponding to the subject's response; and
  (d) system processor means for generating the support surface control signals, receiving the left and right side response measure signals, and automatically diagnosing the presence or absence and side of a balance correction abnormality from the left and right side response measure signals, including classification means for classifying the response measure for each of the left and right sides of the subject as belonging either to a normal group or to one of one or more groups of subjects having pathological responses including means for weighting the left and right side response measures using weightings obtained from a step-wise discriminant analysis on known normal and pathological population groups.

33. A method for diagnosing balance correction abnormalities in a subject, comprising the steps of:
  (a) placing the subject in a standing position on a rotatable support surface capable of rotation in pitch and roll directions;
  (b) rotating the support surface in a plurality of different pitch and roll directions;
  (c) measuring a response of the subject to the rotation of the support surface; and
  (d) displaying the measured response of the subject to the rotation of the support surface.

34. The method of claim 33, wherein the step of measuring a response of the subject to the rotation of the support surface includes the steps of measuring separate left and right side responses of the subject.

35. The method of claim 33, wherein the step of measuring a response of the subject to the rotation of the support surface includes at least one of the steps of:
  (a) attaching a body sway sensor to the subject's body to measure sway of the subject's body in response to rotation of the support surface;
  (b) measuring changes in the subject's center-of-foot pressure or ankle torque in response to rotation of the support surface; and
  (c) measuring the electromyographic responses of a subject's muscle to rotation of the support surface.

36. The method of claim 33, comprising the additional step of diagnosing the presence or absence of a balance correction abnormality from the response measure.

37. The method of claim 36, wherein the step of diagnosing the presence or absence of a balance correction abnormality includes the step of classifying the response measure as belonging either to a normal group or to one of one or more of the groups of subjects having pathological responses selected from the group of groups of subjects having pathological responses consisting of: a vestibular deficit group, a proprioceptive deficit group, a central nervous system lesion group, and an aphysiological group.

38. The method of claim 37, wherein the step of classifying the response measure includes the step of weighting the response measure using a weighting obtained from a step-wise discriminant analysis on known normal and pathological population groups.

39. The method of claim 33, comprising additionally the step of providing feedback of the response measure to the subject.

40. A method for diagnosing balance correction abnormalities in a subject, comprising the steps of:
  (a) placing the subject in a standing position on a support surface capable of rotation in pitch and roll directions;
  (b) rotating the support surface in a plurality of pitch and roll directions;
  (c) measuring left and right side responses of the subject to the rotation of the support surface; and
  (d) diagnosing the presence or absence and side of a balance correction abnormality from the measured left and right side responses.

41. The method of claim 40, wherein the step of diagnosing the presence or absence and side of a balance correction abnormality includes the step of classifying the measured responses for each of the left and right sides of the subject as belonging either to a normal group or to one of one or more of the groups of subjects having pathological responses selected from the group of groups of subjects having pathological responses consisting of: a vestibular deficit group, a proprioceptive deficit group, a central nervous system lesion group, and an aphysiological group.

42. A method for diagnosing balance correction abnormalities in a subject, comprising the steps of:
  (a) placing the subject in a standing position on a support surface capable of rotation in pitch and roll directions;
  (b) rotating the support surface in a plurality of pitch and roll directions;
  (c) measuring left and right side responses of the subject to the rotation of the support surface; and
  (d) diagnosing the presence or absence and side of a balance correction abnormality from the measured left and right side responses, including the step of classifying the measured responses for each of the left and right sides of the subject as belonging either to a normal group or to one of one or more groups of subjects having pathological responses including the step of weighting the left and right side response measures using weightings obtained from a step-wise discriminant analysis on known normal and pathological population groups.

* * * * *